United States Patent [19]
Breault et al.

[11] Patent Number: 5,834,468
[45] Date of Patent: *Nov. 10, 1998

[54] SUBSTITUTED ARYL AND HETEROARYL COMPOUNDS AS E-TYPE PROSTAGLANDIN ANTAGONISTS

[75] Inventors: Gloria Anne Breault, Congleton; John Oldfield, Wilmslow; Howard Tucker; Peter Warner, both of Macclesfield, all of United Kingdom

[73] Assignee: Zeneca Limited, London, United Kingdom

[ * ] Notice: The term of this patent shall not extend beyond the expiration date of Pat. No. 5,811,459.

[21] Appl. No.: 673,878

[22] Filed: Jul. 2, 1996

[30] Foreign Application Priority Data

| Jul. 7, 1995 | [GB] | United Kingdom | 951903 |
| Jul. 7, 1995 | [GB] | United Kingdom | 951923 |
| Jul. 7, 1995 | [GB] | United Kingdom | 9513900 |
| Jul. 7, 1995 | [GB] | United Kingdom | 9513902 |
| Jul. 7, 1995 | [GB] | United Kingdom | 9513924 |
| Jul. 7, 1995 | [GB] | United Kingdom | 9513927 |

[51] Int. Cl.$^6$ .................. A61K 31/495; A61K 31/54; A61K 31/535; A61K 31/33
[52] U.S. Cl. .................. 514/247; 514/255; 514/269; 514/275; 514/256; 514/350; 514/352; 514/354; 514/355; 514/356; 514/438; 514/445; 514/447; 514/461; 514/471; 514/474; 514/535; 514/543; 514/544; 514/617; 514/618; 514/622; 514/619; 514/620; 514/361; 514/365; 514/369; 514/370; 514/374; 514/376; 514/398; 514/399; 514/400; 514/407; 514/403; 562/490; 562/452; 562/433; 562/473; 562/495; 560/8; 560/17; 560/19; 560/43; 560/104; 560/435; 560/183; 564/162; 564/164; 564/182; 564/184; 544/406; 544/407; 544/335; 544/318; 544/319; 544/329; 544/332; 544/224; 544/238; 544/239; 546/299; 546/309; 546/310; 546/315; 546/316; 546/322; 549/64; 549/69; 549/70; 549/71; 549/72; 549/479; 549/480; 549/484; 549/486; 549/487; 548/127; 548/128; 548/129; 548/146; 548/188; 548/194; 548/200; 548/201; 548/215; 548/228; 548/230; 548/233; 548/236; 548/243; 548/245; 548/246; 548/248; 548/316.4; 548/321.5; 548/322.5; 548/323.1; 548/269.4; 548/269.7; 548/272.5; 548/274.1; 548/556; 548/557; 548/562
[58] Field of Search .................. 562/490; 544/406, 544/407, 335, 318, 319, 329, 332, 224, 238, 239; 546/299, 309, 310, 315, 316, 322; 548/127, 128, 129, 146, 188, 194, 200, 201, 215, 228, 230, 233, 236, 243, 245, 246, 248, 316.4, 321.5, 322.5, 323.1, 269.4, 269.7, 272.5, 274.1, 556, 557, 562; 549/64, 69, 70–72, 479, 480, 481, 486, 487; 514/255, 269, 474, 535, 275, 256, 543, 544, 247, 350, 617, 618, 352, 354, 622, 619, 620, 355, 356, 438, 445, 447, 461, 471

[56] References Cited

U.S. PATENT DOCUMENTS

| 3,632,760 | 1/1972 | Shen et al. | 514/211 |
| 3,657,430 | 4/1972 | Shen et al. | 424/230 |
| 4,152,452 | 5/1979 | Douglas et al. | 424/304 |
| 4,277,496 | 7/1981 | Los | 424/309 |
| 4,350,822 | 9/1982 | Albright et al. | 560/45 |
| 4,937,373 | 6/1990 | Carson et al. | 560/56 |
| 5,087,743 | 2/1992 | Janssen et al. | 514/456 |
| 5,105,017 | 4/1992 | Dillard | 568/64 |
| 5,189,033 | 2/1993 | Tucker | 514/211 |
| 5,317,101 | 5/1994 | Oldfield et al. | 514/211 |
| 5,324,743 | 6/1994 | Dillard et al. | 514/211 |
| 5,393,768 | 2/1995 | Dillard | 514/381 |
| 5,409,930 | 4/1995 | Spada et al. | 514/249 |
| 5,420,270 | 5/1995 | Chandrakumar et al. | 540/488 |
| 5,441,950 | 8/1995 | Collins et al. | 514/211 |
| 5,480,883 | 1/1996 | Spada et al. | 514/248 |
| 5,530,157 | 6/1996 | Mewshaw et al. | 562/490 |

FOREIGN PATENT DOCUMENTS

| 2111035 | 6/1994 | Canada . |
| 0000816 | 2/1979 | European Pat. Off. . |
| 094065 | 11/1983 | European Pat. Off. . |
| 122321 | 10/1984 | European Pat. Off. . |
| 0135087 | 3/1985 | European Pat. Off. . |

(List continued on next page.)

OTHER PUBLICATIONS

Brown et al., J. Med. Chem. 1989, 32, 807–826.
Derwent Patent Abstract of DE 1,543,519 (Abstract No. 71–26731S).
Derwent Patent Abstract of DE 2,701,854 (Abstract No. 52629Y/30).
Albright et al., J. Med. Chem. 1983, 26, 1378–1393.
Derwent Patent Abstract of WO 93/23364 (Abstract No. 93–386430/48).
Ames et al., J.C.S. Perkins Transaction 1, (1975) (14) 1390–1395.

*Primary Examiner*—Matthew V. Grumbling
*Attorney, Agent, or Firm*—Paul R. Darkes

[57] ABSTRACT

This invention relates to substituted and unsubstituted [[[(aryl- and heteroaryl-) alkyl-, alkyloxy-, alkylthio-, oxo-, thio-, and alkylamino]- heteroaryl and aryl]- alkylamino-, aminoalkyl-, alkyloxy-, and alkylthio]- aryl and heteroaryl compounds of the formula

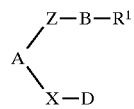

and pharmaceutically acceptable salts thereof, which are useful as antagonists of the pain enhancing effects of E-type prostaglandins, to processes for the preparation of such compounds, to pharmaceutical compositions comprising such compounds, and to methods for treating pain comprising the administration of such compounds.

11 Claims, No Drawings

FOREIGN PATENT DOCUMENTS

| | | |
|---|---|---|
| 0193822 | 9/1986 | European Pat. Off. . |
| 0200101 | 12/1986 | European Pat. Off. . |
| 0218077 | 4/1987 | European Pat. Off. . |
| 0534667 | 3/1991 | European Pat. Off. . |
| 0475206 | 3/1992 | European Pat. Off. . |
| 0480641 | 4/1992 | European Pat. Off. . |
| 0752421 | 1/1997 | European Pat. Off. . |
| 1560281 | 2/1980 | United Kingdom . |
| 1576007 | 10/1980 | United Kingdom . |
| 2041363 | 9/1986 | United Kingdom . |
| WO 92/20642 | 11/1992 | WIPO . |
| WO 96/03380 | 2/1996 | WIPO . |
| WO 96/06822 | 3/1996 | WIPO . |
| WO 96/11902 | 4/1996 | WIPO . |
| WO 97/00863 | 1/1997 | WIPO . |
| WO 97/00864 | 1/1997 | WIPO . |

SUBSTITUTED ARYL AND HETEROARYL COMPOUNDS AS E-TYPE PROSTAGLANDIN ANTAGONISTS

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in pain relief. However both possess undesireable side effects. NSAIDS are known to cause gastrointestinal irritation and oniates are known to be addictive.

We have now found a class of compounds structurally different to NSAII)S and opiates, and useful in the relief of pain.

The compounds of the invention may also possess anti-inflammatory, anti-pyretic and anti-diarrhoeal properties and be effective in other conditions in which prostaglandin $E_2$ ($PGE_2$) wholly or in part plays a pathophysiological role.

According to the invention there is provided a compound the formula I;

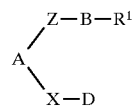

wherein:

A is an optionally substituted: phenyl, naphthyl, pyridyl, pyrazinyl, pyridazinyl, pyrimidyl, thienyl, thiazolyl, oxazolyl,thiadiazolyl having at least two adjacent ring carbon atoms or a bicyclic ring system of the formula:

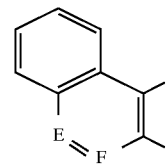

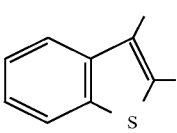

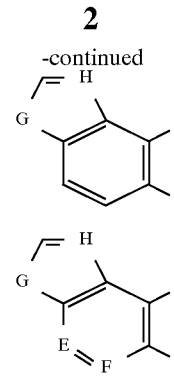

wherein E is nitrogen or CH, F is nitrogen or CH, G is sulphur or oxygen and H is nitrogen or CH;

provided that the —Z—B—$R^1$ and —X—D linking groups are positioned in a 1,2 relationship to one another on ring carbon atoms and the ring atom positioned ortho to the —X— linking group (and therefore in the 3-position relative to the —Z— linking group) is not substituted;

B is an optionally substituted: phenyl, pyridyl, thiazolyl, oxazolyl, thienyl, thiadiazolyl, isoxazole, pyrazole, furyl, pyrrolyl, imidazolyl, pyrazinyl, pyridazinyl, pyrimidyl, pyridone, pyrimidone, pyrazinone or pyridazinone;

D is optionally substituted: pyridyl, pyrazinyl, pyrimidinyl, pyridazinyl, pyrrolyl, thienyl, furyl, imidazolyl, pyrazolyl, thiazolyl, isothiazolyl, oxazolyl, isoxazolyl or phenyl;

$R^1$ is positioned on ring B in a 1,3 or 1,4 relationship with the —Z— linking group in 6-membered rings and in a 1,3-relationship with the —Z— linking group in 5-membered rings and is carboxy, carboxy$C_{1-3}$ alkyl, tetrazolyl, tetrazolyl$C_{1-3}$alkyl, tetronic acid, hydroxamic acid, sulphonic acid, or $R^1$ is of the formula —$SO_2NHR^e$ wherein $R^e$ is hydrogen or $C_{1-6}$alkyl;

or $R^1$ is of the formula (IIA), (IIB) or (IIC):

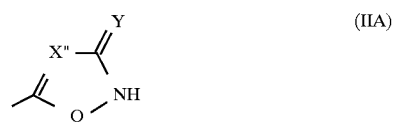

wherein X" is CH or nitrogen, Y is oxygen or sulphur Y' is oxygen or NH, and Z is $CH_2$, NH or oxygen provided that there is no more than one ring oxygen and there are at least two ring heteroatoms; or $R^1$ is of the formula —$CONR^a$ $R^{a1}$ or —$C_{1-3}$alkyl$CONR^aR^{a1}$ wherein $R^a$ is hydrogen, $C_{1-6}$alkyl, $C_{3-7}$cycloalkyl, $C_{3-7}$cycloalkyl$C_{1-3}$alkyl, $C_{5-7}$cycloalkenyl or $C_{5-7}$cycloalkenyl$C_{1-3}$alkyl and $R^{a1}$ is hydrogen, hydroxy or optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkenyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroaryl$C_{1-6}$alkyl, 5- or 6-membered saturated or partially saturated heterocyclyl or 5- or 6-membered saturated or partially saturated heterocyclyl$C_{1-6}$alkyl; or wherein $R^a$ and $R^{a1}$ together with the amide nitrogen to which they are attached $(NR^aR^{a1})$ form an amino acid residue or ester thereof; or $R^1$ is of The formula —CONHSO$_2R^b$ or —$C_{1-3}$alkylCONHSO$_2R^b$ wherein $R^b$ is optionally substituted: $C_{1-10}$alkyl, $C_{2-10}$alkenyl, $C_{2-10}$alkynyl, $C_{3-7}$cycloalkyl, $C_{3-7}$cycloalky$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroylar$C_{1-6}$alkyl, phenyl, phenyl$C_{1-6}$alkyl, 5- or 6-membered saturated or partially saturated heterocyclyl or 5- or 6-membered saturated or partially saturated heterocyclyl$C_{1-6}$alkyl or $R^1$ is of the formula —CONR$^a$N(R$^c$)R$^d$ or —$C_{1-3}$alkylCONR$^a$N(R$^c$)R$^d$ wherein $R^a$ is as hereinabove defined, $R^c$ is hydrogen or $C_{1-6}$alkyl and $R^d$ is hydrogen, hydroxy or optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{5-7}$cycloalkenyl$C_{1-6}$alkyl, $C_{5-7}$cycloalkenyl$C_{2-6}$alkenyl, $C_{5-7}$cycloalkenyl$C_{2-6}$ alkynyl, 5- or 6-membered heteroaryl, 5- or 6-membered heteroaryl$C_{1-6}$alkyl, 5- or 6-membered saturated or partially saturated heterocyclyl, 5- or 6-membered saturated or partially saturated heterocyclyl$C_{1-6}$alkyl, or $R^c$ and $R^d$, together with the nitrogen atom to which they are attached, form a 4 to 8-membered saturated or partially saturated heterocyclic ring or form an amino acid residue or ester thereof;

X is —OCH$_2$-, —SCH$_2$-, —CH$_2$CH$_2$-, CH$_2$-, —O—, —S— or —NH(R$^4$)CH$_2$- wherein the left hand atom is attached to A and the right hand atom is attached to D;

Z is of the formula —CH(R$^3$)CH(R$^3$)N(R$^2$)—, —N(R$^2$)CH(R$^3$)—, —CH(R$^3$)P$^1$—, —(CH(R$^3$))m— or —CH(R$^3$)N(R$^2$)—
wherein
R$^2$ is hydrogen, $C_{1-6}$alkyl (optionally substituted by hydroxy, cyano, nitro, amino, halo, $C_{1-4}$alkanoyl, $C_{1-4}$alkoxy or trifluoromethyl) $C_{2-6}$alkenyl, $C_{2-6}$alkynyl, $C_{3-6}$cycloalkyl, $C_{3-6}$cycloalkyl$C_{1-3}$alkyl, $C_{3-6}$cycloalkyl$C_{2-3}$alkenyl, $C_{5-6}$cycloalkenyl, $C_{5-6}$cycloalkenyl$C_{1-3}$alkyl, $C_{5-6}$cycloalkenyl$C_{2-3}$alkenyl, phenyl, phenyl$C_{1-3}$alkyl or 5- or 6-membered heteroaryl$C_{1-3}$alkyl;
R$^3$ is hydrogen or $C_{1-4}$alkyl;
P$^1$ is oxygen or sulphur, m is 2 or 3 and R$^4$ is hydrogen or $C_{1-4}$alkyl and wherein the left hand atom is attached to A and the right hand atom is attached to B; provided that when Z is —CH(R$^3$)N(R$^2$)— or —(CH(R$^3$))m—, X is not —OCH$_2$-; and N-oxides of —NR$^2$ where chemically possible; and S-oxides of sulphur containing rings where chemically possible; and pharmaceutically acceptable salts and in vivo hydrolysable esters and amides thereof, excluding 4-[4-acetyl-2-benzyl-3-hydroxyphenoxymethyl]-3-methoxybenzoic acid.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclic (heterocyclyl) ring is a ring system having 5 or 6 ring atoms wherein 1,2 or 3 of the ring atoms are selected from nitrogen, oxygen and sulphur.

Particular 5- or 6-membered monocyclic heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring ring systems include pyrrolidinyl, pyrrolinyl, imidazolidinyl, pyrazolidinyl, piperidyl, piperazinyl and morpholinyl.

The linking group —CH(R$^3$)N(R$^2$)CH(R$^3$)— includes —CH$^2$N(R$^2$)CH(Me)—, —CH$_2$N(R$^2$)CH$_2$- and —CH(Me)N(R$^2$)CH$_2$-.

The linking group —CH(R$^3$)CH(R$^3$)N(R$^2$)— includes —CH$_2$CH(Me)N(R$^2$)—, —CH(Me)CH$_2$N(R$^2$)— and —CH$_2$CH$_2$N(R$^2$)—.

The linking group —(CH(R$^3$))m— includes —(CH(Me))$_2$—, —CH$_2$CH(Me)—, —CH(Me)CH$_2$— and —(CH$_2$)$_3$—.

Particular substituents for ring carbon atoms in A and D include halo, trifluoromethyl, nitro, hydroxy, amino, $C_{1-4}$alkylamino, di$C_{1-4}$alkylamino, cyano, $C_{1-6}$alkoxy, —S(O)$_p$C$_{1-6}$alkyl (p is 0, 1 or 2), $C_{1-6}$alkyl (optionally substituted by hydroxy, amino, halo, nitro or cyano), —S(O)$_p$ CF$_3$ (p=0,1 or 2), carbamoyl, $C_{1-4}$alkylcarbamoyl, di($C_{1-4}$alkyl)carbamoyl, $C_{2-6}$alkenyl, $C_{2-6}$alkynyl, $C_{2-4}$alkenylamino, N—$C_{2-4}$alkenyl-N—$C_{1-4}$alkylamino, di-$C_{2-4}$alkenylamino, S(O)pC$_{2-6}$alkenyl, $C_{2-4}$alkenylcarbamoyl, N—$C_{2-4}$alkenyl-N-alkylamino, di-$C_{2-4}$alkenylcarbamoyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, $C_{5-7}$cycloalkenyl$C_{2-3}$alkynyl, $C_{1-4}$alkoxycarbonylamino, $C_{1-4}$alkanoylamino, $C_{1-4}$alkanoyl(N—$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, trifluoro$C_{1-3}$alkylsulphonyl, hydroxyimino $C_{1-6}$alkyl, $C_{1-4}$alkoxyimino$C_{1-6}$alkyl $C_{1-6}$alkylcarbamoylamino, oxazolyl, pyridyl, thiazolyl, pyrimidyl, pyrazinyl and pyridazinyl.

Where a ring nitrogen atom in A can be substituted without becoming quaternised, it is unsubstituted or substituted by $C_{1-4}$alkyl.

Particular substituents for ring carbon atoms in B include halo, amino, $C_{1-4}$alkylamino, di($C_{1-4}$alkyl)amino, trifluoromethyl, nitro, hydroxy, $C_{1-6}$alkoxy, $C_{1-6}$alkyl, cyano, —S(O)pC$_{1-6}$alkyl (p is 0, 1 or 2), carbamoyl, $C_{1-4}$alkylcarbamoyl and di($C_{1-4}$alkyl)carbamoyl.

Where a ring nitrogen atom in B can be substituted without becoming quaternised, it is unsubstituted or substituted by $C_{1-4}$alkyl.

Particular substituents for optionally substituted groups in $R^{a1}$, $R^b$ and $R^d$ include those mentioned above for ring A.

Particular substituents for carbon atoms in optionally substituted groups in $R^{a1}$ include halo, hydroxy, $C_{1-4}$alkyl, nitro, cyano, amino, carboxy, trifluoromethyl, $C_{1-4}$alkoxy, $C_{3-7}$cycloalkyl, $C_{5-7}$cycloalkenyl, $C_{3-7}$cycloalkyl$C_{1-3}$alkyl, $C_{5-7}$cycloalkenyl$C_{1-3}$alkyl, $C_{3-7}$cycloalkyl$C_{2-3}$alkenyl, $C_{5-7}$cycloalkenyl$C_{2-3}$ and $C_{1-4}$alkoxycarbonyl. Particular substituents for optionally substituted groups in $R^b$ include halo, trifluoromethyl, nitro, $C_{1-4}$alkyl, hydroxy, amino, cyano, amino, $C_{1-6}$alkoxy, S(O)pC$_{1-6}$alkyl (p is 0, 1 or 2), carbamoyl, $C_{1-4}$alkylcarbamoyl, di($C_{1-4}$alkyl)carbamoyl, $C_{2-6}$alkenyl, $C_{2-6}$alkynyl, $C_{3-7}$cycloalkyl, $C_{5-7}$cycloalkenyl, $C_{3-7}$cycloalkyl$C_{1-3}$alkyl, $C_{5-7}$cycloalkenyl$C_{1-3}$alkyl, $C_{3-7}$cycloalkyl$C_{2-3}$alkenyl, $C_{5-7}$cycloalkenyl$C_{2-3}$alkenyl, $C_{1-4}$alkoxycarbonylamino, $C_{1-4}$alkanoylamino, $C_{1-4}$alkanoyl(N—$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, hydroxyimino$C_{1-6}$alkyl, $C_{1-4}$alkoxyimino$C_{1-6}$alkyl and $C_{1-6}$alkylcarbamoylamino.

The term alkyl when used herein includes straight chain and branched chain substituents for example methyl, ethyl, n-propyl, isopropyl, n-butyl and isobutyl and functional groups on alkyl chains may be anywhere on the chain, for example hydroxyimino$C_{1-6}$alkyl includes 1-(hydroxyimino)propyl and 2-(hydroxyimino)propyl.

Examples of $C_{1-6}$alkoxycarbonyl are methoxycarbonyl, ethoxycarbonyl and t-butoxycarbonyl; examples of carboxy$C_{1-3}$alkyl are carboxymethyl, 2-carboxyethyl, 1-carboxyethyl and 3-carboxypropyl; examples of $C_{1-6}$alkoxycarbonyl$C_{1-3}$alkyl are methoxycarbonylmethyl, ethoxycarbonylmethyl and methoxycarbonylethyl; examples of tetrazolyl$C_{1-3}$alkyl are tetrazolylmethyl and 2-tetrazolylethyl; examples of $C_{1-4}$alkoxy are methoxy, ethoxy, propoxy and isopropoxy; examples of $C_{2-6}$alkenyl are vinyl and allyl; examples of $C_{2-6}$alkynyl are ethynyl and propynyl; examples of $C_{1-4}$alkanoyl are formyl, acetyl, propionyl and butyryl; examples of halo are fluoro, chloro, bromo and iodo; examples of $C_{1-4}$alkylamino are methylamino, ethylamino, propylamino and isopropylamino; examples of di($C_{1-4}$alkyl)amino are dimethylamino, diethylamino and ethylmethylamino; examples of —$S(O)_p$$C_{1-4}$alkyl are methylthio, methylsulphinyl and methylsulphonyl; examples of $C_{1-4}$alkylcarbamoyl are methylcarbamoyl and ethylcarbamoyl; examples of di($C_{1-4}$alkyl)carbamoyl are dimethylcarbamoyl, diethylcarbamoyl and ethylmethylcarbamoyl; examples of $C_{1-6}$alkyl are methyl, ethyl, propyl and isopropyl; examples of $C_{3-7}$cycloalkyl are cyclopropyl, cyclobutyl and cyclohexyl; examples of $C_{3-7}$cycloalkyl$C_{1-3}$alkyl are cyclopropylmethyl and cyclohexylmethyl; examples of $C_{3-7}$cycloalkyl$C_{2-3}$alkenyl are cyclopropylethenyl and cyclopentylpropenyl; examples of $C_{3-7}$cycloalkyl$C_{2-3}$alkynyl are cyclopropylethynyl and cyclopentylethynyl; examples of $C_{5-7}$alkenyl are cyclopentenyl and cyclohexenyl; examples of $C_{5-7}$cycloalkenyl$C_{1-3}$alkyl are cyclopentenylmethyl and cyclohexenylmethyl; examples of $C_{5-7}$cycloalkenyl$C_{2-3}$alkenyl are cyclohexenylethenyl and cycloheptenylethenyl; examples of $C_{5-7}$cycloalkenyl$C_{2-3}$alkynyl are cyclopentenylethynyl and cyclohexenylethynyl; examples of $C_{1-4}$alkoxycarbonylamino are methoxycarbonylamino and ethoxycarbonylamino; examples of $C_{1-4}$alkanoylamino are acetamido and propionamido; examples of $C_{1-4}$alkanoyl(N—$C_{1-4}$alkyl)amino are N-methylacetamido and N-methylpropionamido; examples of $C_{1-4}$alkanesulphonamido are methanesulphonamido and ethanesulphonamido; examples of $C_{1-4}$alkylaminosulphonyl are methylaminosulphonyl and ethylaminosulphonyl; examples of di($C_{1-4}$alkyl)aminosulphonyl are dimethylaminosulphonyl, diethylaminosulphonyl and ethylmethylaminosulphonyl; examples of $C_{1-4}$alkanoyloxy are acetyloxy and propionyloxy; examples of formyl$C_{1-4}$alkyl are formylmethyl and 2-formylethyl; examples of hydroxyimino$C_{1-6}$alkyl are hydroxyiminomethyl and 2-(hydroxyimino)ethyl; and examples of $C_{1-4}$alkoxyimino$C_{1-6}$alkyl are methoxyiminomethyl, ethoxyiminomethyl and 2-(methoxyimino)ethyl.

Suitable ring systems of the formula (IIA), (IIB) or (IIC) include 5-oxo-4,5-dihydro-1,2,4-oxadiazol-3-yl, 3-oxo-2,3-dihydro-1,2,4-oxadiazol-5-yl, 3-thioxo-2,3-dihydro-1,2,4-oxadiazol-5-yl, 5-oxo-4,5-dihydro-1,3,4-oxadiazol-2-yl, 5-oxo-4,5-dihydro-1,2,4-triazol-3-yl, 3-oxo-2,3-dihydroisoxazol-5-yl, 5-oxo-1,5-dihydroisoxazol-3-yl and 5-oxo-2,3-dihydropyrazol-3-yl.

Amino acid residues formed from $R^a$ and $R^{a1}$ together with the amide nitrogen to which they are attached and esters thereof include for example radicals of the formula —NH—CH($R^c$)—COO$R^d$ wherein $R^c$ is hydrogen, $C_{1-6}$alkyl, $C_{2-6}$alkenyl, $C_{2-6}$alkynyl, phenyl, phenyl$C_{1-3}$alkyl, 5- or 6-membered heteroaryl or 5- or 6-membered heteroaryl$C_{1-3}$alkyl and $R^d$ is hydrogen or $C_{1-6}$alkyl, wherein alkyl, alkenyl, alkynyl, phenyl and heteroaryl groups are optionally substituted. Examples of substituents include those mentioned above for ring A. In particular hydroxy.

When an alkenyl or alkynyl group is directly linked to the nitrogen of a primary or secondary amine it will be appreciated that the double or triple bond may not be in the 1-position. Similarly alkyl groups which are substituted by halo, hydroxy or an amine may not be substituted by these substituents in the 1-position when the alkyl group is directly linked to the nitrogen of a primary or secondary amine.

Preferably A is an optionally substituted: phenyl, naphthyl, pyridyl, pyrazinyl, pyridazinyl, pyrimidyl, thienyl, thiazolyl, oxazolyl or thiadiazolyl having at least two adjacent ring carbon atoms;

More preferably A is optionally substituted: phenyl, naphthyl, thiadiazolyl, thienyl, pyridyl or pyrimidyl.

Most preferably A is optionally substituted: phenyl or thienyl.

In particular A is optionally substituted phenyl.

Preferably B is optionally substituted: pyridyl, phenyl, thiazolyl, thienyl, pyridazinyl, thiadiazolyl, imidazolyl, pyrazinyl, pyrimidyl, or oxazolyl.

More preferably B is optionally substituted: pyridyl, phenyl, thiazolyl, thienyl, pyridazinyl or oxazolyl.

Yet more preferably B is optionally substituted: pyridyl, phenyl, thienyl, pyridazinyl or thiazolyl.

Yet more preferably B is optionally substituted: phenyl, pyridyl or pyridazinyl.

Most preferably B is pyridazinyl.

Preferably D is optionally substituted: pyridyl, thienyl, thiazolyl, furyl or phenyl.

More preferably D is optionally substituted: thienyl, furyl or phenyl.

Most preferably D is optionally substituted phenyl.

Preferred optional substituents for ring carbon atoms in A, are halo, nitro, trifluoromethyl, cyano, amino, $C_{1-6}$alkoxy, carbamoyl, $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, $C_{1-4}$alkylcarbamoyl, di($C_{1-4}$alkyl)carbamoyl, $C_{1-4}$alkanoylamino, $S(O)_p$$C_{1-6}$alkyl, $C_{1-4}$alkanesulphonamido, benzenesulphonamido, $C_{1-6}$alkanoyl, $C_{1-4}$alkoxyimino$C_{1-4}$alkyl and hydroxyimino$C_{1-4}$alkyl.

Most preferred optional substituents for ring carbon atoms in A are chloro, bromo and methanesulphonyl.

In particular A is substituted on a ring carbon atom by bromo.

Preferably, when A is a 6-membered ring, A is unsubstituted or substituted in the 4-position relative to the —X— linking group.

Preferred optional substituents for ring carbon atoms of B are halo, amino, di$C_{1-4}$alkylamino, $C_{1-4}$alkylamino, trifluoromethyl, nitro, hydroxy, methyl, $C_{1-4}$alkyl, $C_{1-4}$alkoxy and cyano.

More preferred optional substituents for ring carbon atoms of B are fluoro, chloro, bromo, trifluoromethyl, hydroxy, methyl, methoxy and cyano.

Preferably D is optionally substituted by 1 or 2 substituents selected from halo, trifluoromethyl, nitro, hydroxy, amino, $C_{1-4}$alkylamino, di($C_{1-4}$alkyl)amino, cyano, $C_{1-6}$alkoxy, —S(O)$_p$$C_{1-4}$alkyl (p is 0, 1 or 2), $C_{1-4}$alkanoyl, $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, wherein $C_{3-7}$cycloalkyl, $C_{5-7}$cycloalkenyl, $C_{1-6}$alkyl and $C_{1-6}$alkyloxy are optionally substituted by trifluoromethyl, hydroxy, halo, nitro, cyano or amino.

Most preferred optional substituents for D include halo, nitro, hydroxy, cyano, $C_{1-6}$alkyl, amino, $C_{1-6}$alkoxy or carbamoyl. Most preferably D is unsubstituted.

Preferably A is unsubstituted or substituted by one substituent.

Preferably B is unsubstituted or substituted by one substituent.

Preferably $R^1$ is carboxy, carbamoyl, tetrazolyl or of the formula —CONR$^a$R$^{a1}$ or —CONHSO$_2$R$^b$.

Preferably, $R^{a1}$ is hydrogen, hydroxy or optionally substituted: $C_{1-6}$alkyl, $C_{2-6}$alkenyl, $C_{2-6}$alkynyl, cyclopropyl$C_{1-4}$ alkyl, cyclobutyl$C_{1-4}$alkyl, cyclopentyl$C_{1-4}$ alkyl, cyclohexyl$C_{1-4}$alkyl, pyridyl$C_{1-4}$alkyl, pyrimidyl$C_{1-4}$ alkyl, pyrazinyl$C_{1-4}$alkyl, furyl$C_{1-4}$alkyl, pyridazinyl$C_{1-4}$ alkyl, tetrazolyl$C_{1-4}$alkyl, pyrrolidinyl$C_{1-4}$alkyl, morpholinyl$C_{1-4}$alkyl, imidazolium$C_{1-4}$alkyl, N-methylimidazolium$C_{1-4}$alkyl, pyridinium$C_{1-4}$alkyl, pyridyl, pyrimidyl, pyrazinyl, pyridazinyl, N-methylpyrimidinium, N-methylimidazolyl, pyridinium, pyrimidinium, tetrazolyl, phenyl, cyclopropyl, cyclobutyl, cyclopentyl, cyclohexyl, cyclopentenyl, cyclohexenyl, cycloheptenyl, cyclopentenyl$C_{1-4}$alkyl, cyclohexenyl$C_{1-4}$alkyl or cycloheptenyl$C_{1-4}$alkyl.

More preferably $R^{a1}$ is hydrogen, $C_{1-6}$alkyl (optionally substituted by halo, hydroxy, nitro, cyano, amino, carboxy, $C_{1-4}$-alkoxycarbonyl), pyridyl$C_{1-4}$alkyl, pyrimidyl$C_{1-4}$alkyl, pyrazinyl$C_{1-4}$alkyl, furyl$C_{1-4}$alkyl, pyridazinyl$C_{1-4}$alkyl, tetrazolyl$C_{1-4}$alkyl, or $C_{2-6}$alkenyl.

Most preferably $R^{a1}$ is $C_{1-4}$alkyl (optionally substituted by one or two substituents selected from hydroxy, carboxy and $C_{1-4}$alkoxycarbonyl), pyridyl$C_{1-4}$alkyl and furyl$C_{1-4}$alkyl.

Preferably —$C_{1-3}$alkylCONR$^a$R$^{a1}$ is —CH$_2$CONR$^a$R$^{a1}$.

Preferably —$C_{1-3}$alkylCONHSO$_2$R$^b$ is —CH$_2$CONHSO$_2$R$^b$.

Preferably —$C_{1-3}$alkylCONR$^a$NR$^c$R$^d$ is —CH$_2$CONR$^a$NR$^c$R$^d$.

Preferably $R^b$ is optionally substituted: $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, 5- or 6-membered heteroaryl$C_{1-3}$alkyl, 5- or 6-membered saturated or partially saturated heterocyclyl$C_{1-3}$alkyl, phenyl$C_{1-3}$alkyl, phenyl, 5- or 6-membered heteroaryl or 5- or 6-membered saturated or partially saturated heterocyclyl.

More preferably $R^b$ is $C_{1-4}$alkyl (optionally substituted by hydroxy, nitro, cyano, amino, $C_{1-4}$alkylamino, di-$C_{1-4}$alkylamino, $C_{1-4}$alkanoylamino, carbamoyl, $C_{1-4}$alkyl-N—$C_{1-4}$alkanoylamino, carbamoyl, $C_{1-4}$alkylcarbamoyl, di-$C_{1-4}$alkanoylcarbamoyl, halo, $C_{1-4}$alkoxy) or optionally substituted phenyl$C_{1-3}$alkyl, pyridyl$C_{1-3}$alkyl, phenyl, thienyl, thiadiazolyl, oxazolyl, isoxazolyl, pyrazolyl or 1,1-dioxidotetrahydrothienyl.

Most preferably $R^b$ is $C_{1-4}$alkyl, hydroxy$C_{1-4}$alkyl, $C_{1-4}$alkoxy$C_{1-4}$alkyl, phenyl (optionally substituted by halo, cyano, nitro, carbamoyl, $C_{1-4}$alkylcarbamoyl, di-$C_{1-4}$alkylcarbamoyl, hydroxy, amino, $C_{1-4}$alkanoylamino, N—$C_{1-4}$alkanoyl-N—$C_{1-4}$alkylamino, $C_{1-4}$alkylamino or di—($C_{1-4}$alkyl)amino), benzyl (optionally substituted by halo, cyano, nitro, carbamoyl, $C_{1-4}$alkylcarbamoyl, di-$C_{1-4}$alkylcarbamoyl, hydroxy, amino, $C_{1-4}$alkanoylamino, N—$C_{1-4}$alkanoyl-N—$C_{1-4}$alkylamino,$C_{1-4}$alkylamino or di-($C_{1-4}$alkyl)amino), thiadiazolyl (optionally substituted by $C_{1-4}$alkanoylamino, amino, $C_{1-4}$alkylamino or di-$C_{1-4}$ alkylamino), thienyl (optionally substituted by halo or pyridyl), isoxazolyl (optionally substituted by $C_{1-4}$alkyl or halo), pyrazolyl (optionally substituted by $C_{1-4}$alkyl or halo) or 1,1-dioxidotetrahydro-2-thienyl.

Preferably $R^c$ is hydrogen and $R^d$ is 5- or 6-membered heteroaryl or $R^c$ and $R^d$, together with the nitrogen atom to which they are attached, form a 5- or 6-membered saturated or partially saturated heterocyclic ring.

More preferably $R^c$ is hydrogen and $R^d$ is pyridyl or $R^c$ and $R^d$, together with the nitrogen atom to which they are attached, form morpholino.

Preferably $R^1$ is carboxy, carbamoyl, tetrazolyl or of the formula —CONR$^a$R$^{a1}$ or —CONHSO$_2$R$^b$.

Most preferably $R^1$ is carboxy.

More preferably $R^2$ is hydrogen, methyl, ethyl, cyclopropylmethyl, 2-fluoroethyl, 2,2-difluoroethyl, 2,2,2-trifluoroethyl, cyanomethyl, allyl or 2-propynyl.

Most preferably $R^2$ is hydrogen, ethyl, allyl or 2-propynyl.

In particular $R^2$ is hydrogen or ethyl.

Preferably $R^3$ is hydrogen, methyl or ethyl.

Most preferably $R^3$ is hydrogen.

Most preferably $R^4$ is hydrogen.

In one aspect A is optionally substituted: naphthyl, pyridyl, pyrazinyl, pyridazinyl, pyrimidyl, thienyl, thiazolyl, oxazolyl, thiadiazolyl having at least two adjacent ring carbon atoms or a bicyclic ring system of the formula:

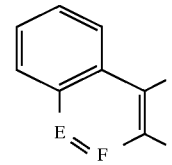

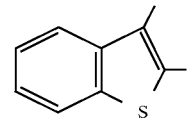

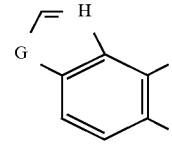

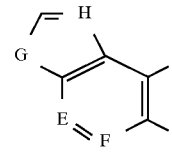

wherein E is nitrogen or CH, F is nitrogen or CH, G is sulphur or oxygen and H is nitrogen or CH.

In another aspect A is optionally substituted phenyl.

Preferably m is 2.

In one aspect $P^1$ is oxygen.

In another aspect $P^1$ is sulphur.

Preferably $R^4$ is hydrogen, methyl or ethyl.

Most preferably $R^4$ is hydrogen.

When —Z— is —CH($R^3$)$P^1$—, —CH($R^3$)CH($R^3$)N($R^2$)— or —N($R^2$)CH($R^3$)—,
—X— is preferably —OCH$_2$—.

When —Z— is —[CH($R^3$)]m—, —X— is preferably —CH$_2$CH$_2$— or —NHCH$_2$—.

When —Z— is —CH($R^3$)N($R^2$)—, —X— is preferably —CH$_2$CH$_2$—, —CH$_2$—, —O— or —NHCH$_2$—.

A preferred class of compounds is that of the formula (II):

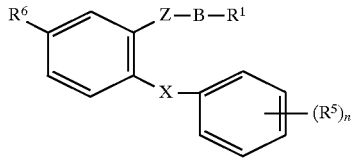

wherein
Z, X, $R^1$ and $R^2$ are as hereinabove defined, n is 0 or 1, $R^5$ is hydrogen or as hereinabove defined for substituents for ring carbon atoms in D, $R^6$ is hydrogen or as hereinabove defined for substituents for ring carbon atoms in A and B is phenyl, thienyl, pyridazinyl, pyridyl, or thiazolyl.

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses pain relieving properties. The synthesis of optically active forms may be carried out by standard techniques of organic chemistry well known in the art, for example by synthesis from optically active starting materials or by resolution of a racemic form. Similarly, pain relieving properties may be evaluated using the standard laboratory techniques referred to hereinafter.

An in vivo hydrolysable ester of a compound of the formula (I) containing carboxy group is, for example, a pharmaceutically acceptable ester which is hydrolysed in the human or animal body to produce the parent acid, for example, a pharmaceutically acceptable ester formed with a (1-6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), (1-4C)alkyl (such as methyl) or (1-4C) alkoxy (such as ethoxy) group. The term also includes ot-acyloxyalkyl esters and related compounds which breakdown to give the parent hydroxy group. Examples of α-acyloxyalkyl esters include acetoxymethoxycarbonyl and 2,2-dimethylpropionyloxymethoxycarbonyl.

An in vivo hydrolysable ester of a compound of the formula (I) containing a hydroxy group is, for example, a pharmaceutically acceptable ester which is hydrolysed in the human or animal body to produce the parent alcohol. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable value for an in vivo hydrolysable amide of a compound of the formula I containing a carboxy group is, for example, a N-(1-6C)alkyl or N,N-di-(1-6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula (I) is, for example, an acid-addition salt of a compound of the formula (I) which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

In a further aspect the invention provides a process for preparing compounds of the formula (I) or pharmaceutically acceptable salts or in vivo hydrolysable amides or ester thereof, which comprises deprotecting a compound of the formula (III):

wherein $R^7$ is $R^1$ or protected $R^1$, —$Z^1$— is —Z— or protected —Z—, $R^2$, $R^3$, Z, X, A, B and D are as hereinabove defined, and any optional substituents are optionally protected and at least one protecting group is present; and thereafter if necessary;
   i) forming a pharmaceutically acceptable salt;
   ii) forming an in vivo hydrolysable ester or amide;
   iii) converting one optional substituent into another optional substituent.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenylsilyl), a diaryl-(1-4C)alkylsilyl group (especially tert-butyldiphenylsilyl), a (1-4C)alkyl group (especially methyl), a (2-4C)alkenyl group (especially allyl), a (1-4C)alkoxymethyl group (especially allyl), a (1-4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1-4C) alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2-4C) alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2-4C)alkanoyl group (especially acetyl), a (1-4C) alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1-4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (III) may be prepared by:

a) when —$Z^1$— is —CH($R^3$)NHCH($R^3$)—, —CH($R^3$) CH($R^3$)NH—, —CH($R^3$)NH— or —NHCH($R^3$)— reducing a compound of the formula (IVa) or (IVb):

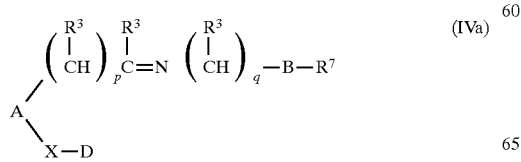

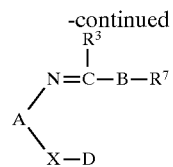

b) when —$Z^1$— is —CH($R^3$)N($R^8$)CHR$^3$), —CH($R^3$)CH ($R^3$)N($R^8$)— or —CH($R^3$)N($R^8$)— and B is an activated heterocycle and $R^8$ is hydrogen or $C_{1-6}$alkyl, reacting a compound of the formula (V) with a compound of the formula (VI):

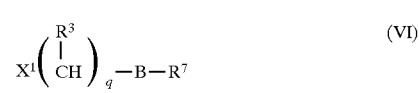

c) converting $R^{10}$ to $R^7$ in a compound of the formula (VII):

d) when —$Z^1$— is —CH($R^3$)N($R^8$)—, —N($R^8$)CH ($R^3$)— or —CH($R^3$)CH($R^3$)N($R^8$)— and $R^8$ is other than hydrogen, reacting a compound of the formula $R^8X^2$ with a compound of the formula (VIII):

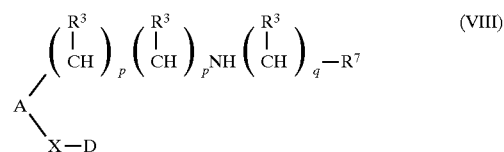

e) when —$Z^1$— is —CH($R^3$)N($R^8$)CH($R^3$)—, —CH($R^3$) CH($R^3$)N($R^8$)— or —CH($R^3$)N($R^8$)—, reacting a compound of the formula (IX) with a compound of the formula (X):

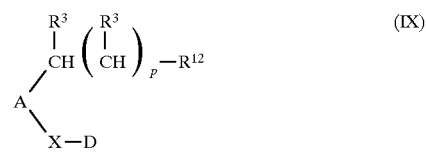

f) when X is —CH$_2$CH$_2$-, reducing a compound of the formula (XIA) or (XIB):

g) when X is —CH$_2$-, hydrogenating a compound of the formula (XII):

h) when X is —CH$_2$—, reacting a compound of the formula (XIII) with a compound of the formula X$^3$-D

i) when X is —O—, reacting a compound of the formula (XIV) with a compound of the formula X$^5$-D:

j) when X is —NHCH$_2$—, reacting a compound the formula (XV) with a compound of the formula X$^7$CH$_2$D or D-CHO:

k) when X is —OCH$_2$—, reacting a compound of the formula L$^1$—CH$_2$D with a compound of the formula (XVI):

l) when X is —N(R$^4$)CH$_2$—, reacting a compound of the formula (XVII) with a compound of the formula R$^4$X$^8$:

m) when —Z$^1$— is of the formula —CH(R$^3$)CH$_2$N(R$^8$)—, reducing a compound of the formula (XVIII)

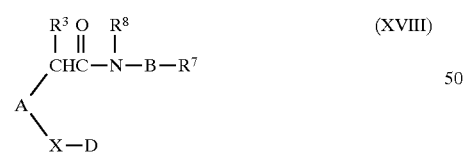

n) when —Z$^1$— is of the formula —[CH(R$^3$)]m—, by reducing a compound of the formula (XIXa) or (XIXb):

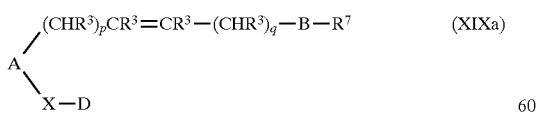

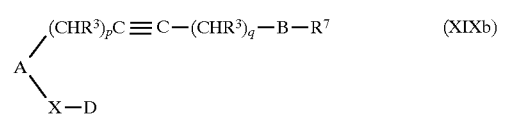

o) when —Z$^1$— is of the formula —[CH(R$^3$)]m—, and m is 3, by reducing a compound of the formula (XX):

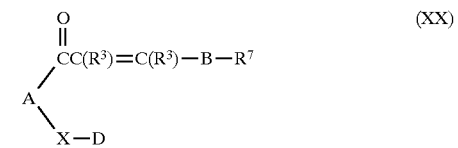

p) when —Z$^1$— is of the formula —[CH(R$^3$)]m—, and B is an activated heterocycle by acting a compound of the formula (XXI) with a compound of the formula (XXII):

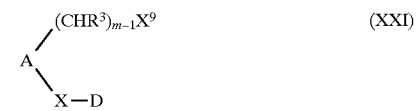

R$^3$CH$_2$—B—R$^7$    (XXII)

q) when —Z$^1$— is of the formula —CH(R$^3$)P$^1$—, reacting a compound of the formula HP$^1$—B—R$^7$ with a compound of the formula (XXIII):

r) when —Z$^1$— is of the formula —CH(R$^3$)P$^1$—, reacting a compound of the formula X$^{14}$—B—R$^7$ with a compound of the formula (XXIV):

s) when —Z$^1$— is of the formula —N(R$^3$)CH(R$^8$)—, reacting a compound of the formula (XXV) with a compound of the formula (VI):

wherein R$^3$, R$^7$, Z$^1$, A, B, D and X as hereinabove defined, R$^8$ is R$^2$ or protected R$^2$, X$^1$ is a leaving group, R$^{10}$ is a precursor of R$^7$, X$^2$ is a leaving group, R$^{11}$ is a removable activating group, R$^{12}$ is a leaving group, either X$^3$ is a leaving group and X$^4$ is ZnX$^3$ or X$^4$ is a leaving group and X$^3$ is ZnX$^4$, either X$^5$ is a leaving group and X$^6$ is hydroxy or X$^6$ is hydroxy and X$^5$ is a leaving group, L$^1$, X$^7$ X$^8$, X$^9$, X$^{13}$ and X$^{14}$ are leaving groups and p and q are independently 0 or 1 provided that p and q are not both 1; and thereafter if necessary:
i) removing any protecting groups;
ii) forming a pharmaceutically acceptable salt;
iii) forming an in vivo hydrolysable ester or amide;
iv) converting an optional substituent into another optional substituent.

Particular values for leaving groups include halogen, for example, chloro, bromo and iodo, sulphonates, for example tosylate, p-bromobenzenesulphonate, p-nitrobenzenesulphonate, fluorosulphonate, methanesulphonate and triflate or phosphoric esters such as a diarylphosphoric ester.

Compounds of the formula (IVa) and (IVb) can be reduced using agents such as sodium borohydride or sodium cyanoborohydride. The compounds of the formula (IVa) may be prepared by reacting a compound of the formula (X) with a compound of the formula (XVa1)

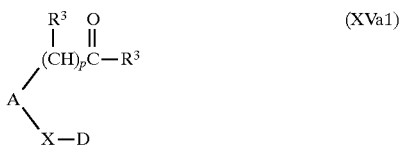

wherein A, X, D and p are as hereinabove defined.

The reaction between compounds of the formulae (X) and (IVa1) may be carried out under standard conditions known in the art for the formation an imine (Schiffs base), which can be reduced in situ. For example imine formation and reduction in situ ma,t be carried out in an inert solvent such as toluene or tetrahydrofuran, in the presence of a reducing agent such as sodium cyanoborohydride (NaCNBH$_3$) under acidic conditions (Synthesis 135, 1975; Org. Prep. Proceed. Int. 11, 201, 1979). When p is 1 and R$^3$ is hydrogen, compounds of the formula (IVa1) may be prepared by reducing a compound of the formula (XVIIIA)—see scheme 1.

The compounds of the formula (IVb) may be formed by reacting a compound of the formula R$^7$—B—C(=O)R$^3$ with a compound of the formula (IVb1)

and reducing the product in situ, wherein A, D and X are as hereinabove defined.

The reaction between compounds of the formulae R$^7$—B—C(=O)—R$^3$ and (IVb1) is normally carried out as reductive alkylation. In this reaction the compound of the formula (IVb1) is reduced to the related amine, which reacts with the compound of the formula R$^7$—B—C(=O)—R$^3$ to give a compound of the formula (IVb) which is immediately reduced to a compound of the formula (I) or (III) in situ. Alternatively one or more steps could be performed separately. Palladium-on-carbon is commonly used as the reducing agent in this reaction.

Compounds of the formulae (V) and (VI) may be reacted together under standard conditions for example, in an aprotic solvent such as DMF in the presence of a weak base, in a temperature range of ambient to 180° C. Suitable bases include sodium hydrogen carbonate and amide bases such as Hunig's base, N-ethyl-N,N-diisopropylamine, tributylamine or 1,8-diazabicyclo[5.4.0]undec-7-ene (DBU). Suitable values for X$^1$ include, halo, tosylate, mesylate and triflate. In particular X$^1$ is chloro or bromo.

In general this process is best used when ring B is an electron poor heterocycle such as pyridine, pyrimidine, pyridazine or pyrazine.

Compounds of the formula (V) wherein p is 1 are conveniently prepared from compounds of the formula (VA) as shown in scheme 1. Compounds of the formula (VB) in which X$^{15}$ is a leaving group, such as bromo, are reacted with a cyanide salt such as potassium cyanide in a solvent such as DMF, in a temperature range of 20°–140° C. to give a compound of the formula (VC). 18 Crown 6 may be added as a catalyst. The compound of the formula (VC) may be reduced by catalytic hydrogenation with, for example, palladium on carbon, borane.THF, borane.DMS complexes, lithium aluminium hydride or lithium borohydide/trimethylsilyl chloride to give a compound of the formula (VA). Alternatively, a compound of the formula (VD) may be prepared by reacting the compound of the formula (VE) with CH$_3$NO$_2$ in the Henry reaction. The reaction is performed in the presence of an amine base such as triethylamine, in THF or CH$_3$NO$_2$ as solvent, in a temperature range of 0°–20° C. The compound of the formula (VD) may then be reduced with a strong reducing reagent such as lithium aluminium hydride or by hydrogenation with palladium-on-carbon as the catalyst, to give a compound of the formula (VA). When R$^8$ is other than hydrogen, compounds of the formula (V) may be prepared by alkylating the compound of the formula (VA) using a similar reaction to that described in process d).

Particular values for R$^{10}$ include cyano, carbamoyl, alkoxycarbonyl, carboxy and activated carboxy groups such as acid chlorides and activated esters.

The cyano group may be converted into a tetrazole ring by reacting it with, for example, ammonium or tin azide in an aprotic solvent such as DMF, in a temperature range of 100° C. to 130° C. For further information on tetrazole synthesis see S. J. Wittenberger and B. J. Donner JOC, 1993, 58, 4139–4141; BE Huff et al, Tet. Lett, 1993, 50, 8011–8014; and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out in neat formic acid or neat trifluoroacetic acid optionally in an organic solvent such as dichloromethane.

An alkoxycarbonyl or an activated carboxy group, such as an acid chloride or activated ester, or an acyl group such as an alkanoyl group may be converted to an amide group by reacting it with the appropriate amine in an inert solvent such as DMF or dichloromethane, in a temperature range of 0° C. to 150° C., preferably around ambient temperature, in the presence of a base such as triethylamine.

The compounds of the formulae (VIII) and R$^8$X$^2$ may be reacted together in an aprotic solvent such as DMF in the presence of a base such as sodium carbonate or sodium hydride. Suitable values for X$^2$ are halo, tosylate, mesylate and triflate, in particular halo such as iodo.

The reaction between compounds of the formulae (IX) and (X) is conveniently carried out under mild conditions known for the Mitsunobu reaction (Mitsunobu, O. Synthesis 1981, 1), for example in the presence of di (C$_{1-4}$alkyl) azocarboxylate and triphenylphosphine or 1$^1$,1$^1$—(azodicarbonyl)dipiperidine and tributylphosphine (Tet. Lett. 34, 1993, 1639–1642) in an inert solvent such as toluene, benzene, tetrahydrofuran or diethylether, in particular toluene. Examples of removable activating groups are tert-butyloxycarbonyl and trifluoroacetyl.

Furthermore the alkoxycarbonyl groups can be removed by hydrolysis of the ester to leave the unprotected amino group and trifluoroacetyl groups can be reduced to 2,2,2-trifluoroethyl.

When R$^8$ is alkoxycarbonyl and R$^{12}$ a leaving group such as tosylate, mesylate, chloro, bromo or iodo, the compounds of the formula (IX) and (X) can be reacted together to form a compound of the formula (I) or (III), in the presence of a strong base such as sodium hydride, potassium hydride, potassium tert-butoxide, lithium diisopropyl amine or LiN(SiMe$_3$)$_2$, in DMF or an etherial solvent such as diethyl ether or THF, in a temperature range of −78° C. to ambient temperature.

Compounds of the formula (IX) wherein p is 1 are conveniently prepared from a compound of the formula (IXA)—see scheme 1. For example by reacting the compound of the formula (IXA) with tosyl or mesyl chloride or using Mitsunobu reagents.

Compounds of the formula (IXA) may be formed as shown in scheme 1, from compounds of the formulae (VD) or (IXB).

Compounds of the formula (VD) may be converted to compounds of the formula (IXA) by either sequential treatment with Bu$_3$SnH, ozone and sodium borohydride, (Tet Lett (1987), 28, 53, 67) or, hydrogenation with Pd/C (or other catalysts to the RCH$_2$CH$_2$NO$_2$) followed by the Nef reaction [conditions for the Nef reaction include aqueous TiCl$_3$, or 30% H$_2$O$_2$/K$_2$CO$_3$ (Nef reaction is detailed in March, Advanced Organic Chemistry)] and sodium borohydride reduction, to give the aldehyde (RCH$_2$CHO).

Compounds of the formula (IXB) are prepared by reacting a compound of the formula (IXC) with a compound of the formula CH$_2$=CHM, wherein M is trialkyltin, magnesium halide or di(alkoxy)borane/weak base (for example potassium or caesium carbonate) in the presence of a catalytic amount of palladium (0). The magnesium and tin reactions are conveniently performed in anhydrous THF. The compound of the formula (IXB) is conveniently converted to the alcohol (IXA) by reacting it with catechol borane followed by treatment with hydrogen peroxide.

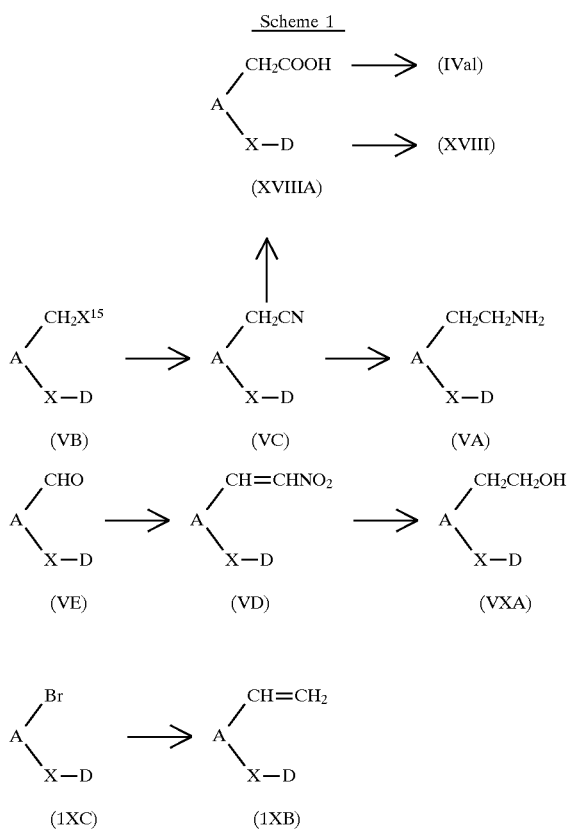

Compounds of the formula (X) are conveniently prepared from compounds of the formula H$_2$N—(CH(R$^3$))$_q$—B—R$^7$ wherein B and R$^7$ are as hereinabove defined. R$^8$ may be introduced using a similar reaction to that of process d) and R$^{11}$ may be introduced by standard methods known in the amino-protecting group art.

Compounds of the formula NH$_2$(CH(R$^3$))$_q$—B—R$^7$ are generally known in the art or can be prepared from related compounds having other functional groups in place of the amino group. For example, a compound of the formula NO$_2$(CH(R$^3$))$_q$—B—R$^7$ may be reduced to the amino group.

The compounds of the formula (XIa) and (XIb) may be reduced under standard conditions known in the art for the reduction of olefins, and acetylenes, for example, catalytic hydrogenation using Raney nickel, platinum metal or its oxide, rhodium, zinc oxide, palladium-on-charcoal or Wilkinson's catalyst [RhCl(Ph$_3$P)$_3$] as the catalyst. When halo groups are present in the compounds of the formula (XIa) or (XIb), Wilkinson's catalyst is preferred.

Catalyst hydrogenation is conveniently carried out in the temperature range 0° C. to 150° C., but preferably at ambient temperature at slightly above atmospheric pressure, unless the double bond is highly substituted in which case higher temperatures and pressure may be required, or Wilkinson's catalyst in which case a temperature of approximately 50° C. and pressure of approximately 50 atmospheres are preferable.

Compounds of the formula (XIa) can be prepared using a Wittig or Homer-Emmons reagent. For example, compounds of the formula (XIa1) and (XIa2) may be reacted together in an inert solvent such as hexane, tetrahydrofuran or diethyl ether in a temperature range of −78° C. to ambient.

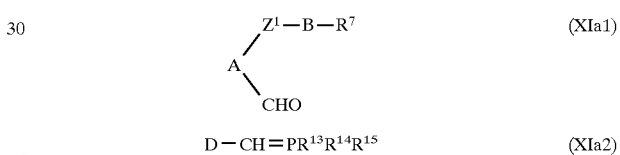

wherein R$^{13}$—R$^{15}$ are independently C$_{1-6}$alkyl or optionally substituted phenyl.

Preferably R$^{13}$—R$^{15}$ are all the same. In particular R$^{13}$—R$^{15}$ are all phenyl.

The compounds of the formula (XIa2) are rarely isolatable and usually prepared in situ by deprotonating a compound of the formula (XIa3) (scheme I). Deprotonation is usually carried out in an inert solvent such as tetrahydrofuran or diethyl ether, in a temperature range of −78° C. to ambient, in the presence of a strong base. Examples of strong bases are lithium hexamethyldisilylamide, CH$_3$SOCH$_2$—Na$^+$ and butyl lithium.

Compounds of the formula (XIa3) may be prepared by reacting a compound of the formula (XIa4) with a compound of the formula (XIa5) (scheme I). Suitable values for L$^{11}$ include halogen, such as chloro, bromo or iodo. Typically an inert solvent such as acetonitrile, diethyl ether, tetrahydrofuran or toluene is used and a temperature range of 50° C. or 120° C. The compounds of the formula (XIa4) may be known or prepared from another compound of the formula (XIa4) or a compound of the formula D—CHO wherein D is as hereinabove defined. For example the compound of the formula D—CHO may be reduced to a compound of the formula (XIa4) wherein L$^{11}$ is hydroxy. A compound of the formula (XIa4), wherein L$^{11}$ is hydroxy, may then be converted to a compound of the formula (XIa4) wherein L$^{11}$ is bromo by, for example, bromonating with tetrabromomethane/triphenylphosphine or tribromophosphine.

Scheme 2

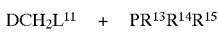

(XIa4)    (XIa5)

(XIa3)

wherein D, $R^{13}$—$R^{15}$ and $L^{11}$ are as hereinabove defined.

Alternatively, compounds of the formula (XIa) can be prepared by dehydrating a compound related to a compound of the formula (I) or (III) in which X is —CH(OH)CH$_2$—. Dehydration is conveniently carried out using standard methods known in the art, for example, at elevated temperatures in the presence of sulphuric acid, phosphoric acid or aluminium oxide. Alternatively, the hydroxy group may be converted to a bromo group. The alkene can then be formed by treatment with a strong base such as sodium hydride or LDA.

The compounds in which X is —CH(OH)CH$_2$—may be prepared by reacting a compound of the formula (XIa1) with D—CH$_2$ in the form of a zinc or Grignard reagent. Reaction conditions for these common reactions are known in the art. For example by reacting DCH$_2$X$^8$, wherein X$^8$ is a leaving group such as bromo or iodo, with zinc or magnesium as appropriate in an inert solvent such as ether or THF, in a temperature range of 0° C. to reflux. The reaction can be initiated by the introduction of iodine or 1,2-dibromomethane if necessary. When ester groups are present in one or other of the reagents, the zinc reaction is preferred.

Compounds of the formula (XIb) are conveniently prepared by reacting a compound of the formula (XIb 1) with a D—X$^7$Cu(I) salt, wherein X$^7$ is a leaving group under conditions known for the Heck reaction:

The reaction is performed in the presence of palladium(0) catalyst, such as Pd(PPh$_3$)$_4$ or Pd(OAc)$_2$ which form the active Pd(0) catalyst in situ. Other palladium(0) catalysts are known in the art. Suitable leaving groups may be chosen from bromo, chloro, iodo, trifluoromethylsulphonyloxy or fluorosulphonate.

Compounds of the formula (XIb1) can be formed by reacting a compound of the formula (XIb2) with a compound of the formula CH≡C—TMS or CH≡CC(Me)$_2$OH:

wherein TMS is trimethylsilyl and X$^{10}$ is a leaving group. This coupling reaction is performed in an inert solvent, such as dimethylformamide, tetrahydrofuran or NMP, in the presence of palladium(0), copper (I) in the form of a salt such as the halide or triflate and a base such as triethylamine, tributylamine, 1,8-diazobicyclo[5.4.0]undec-7-ene (DBU) or potassium acetate.

It is not always convenient to form the acetylene lower link in intermediates containing the upper —Z$^1$—B—R$^7$ group, because certain groups may be sensitive to the reaction conditions. It may therefore be more appropriate to form the acetylene link prior to the introduction of the upper link using processes and intermediates related to those of processes a), b), e), m), n), o), p), q), or r) and their precursor processes.

The hydrogenation of the compound of the formulae (XII) is performed under standard conditions known in the art. Examples of the catalytic hydrogenation agents are given above in the discussion of the reduction of compounds of the formula (XIa) and (XIb).

Compounds of the formula (XII) may be formed by reacting a compound of the formula D—CHO or

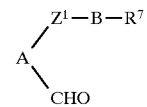

with the appropriate zinc or Grignard reagent [R$^7$—Z$^1$—A$^-$ and D$^-$respectively] under conditions known in the art for these reactions.

Compounds of the formulae (XIII) and X$^3$—D are conveniently reacted together in a polar aprotic solvent such as dimethylformamide, tetrahydrofuran or NMP in the presence of palladium(0) or nickel(0) as catalyst.

The reaction between the compound of the formula (XIV) and the compound of the formula X$^5$—D is conveniently a copper mediated oxygen-arylation reaction. The reaction is carried out in an inert solvent such as dimethylformamide or N-methylpyrrolidone (NMP) in the present of a Cu(1)X$^6$ salt and a weak base such as potassium carbonate or caesium carbonate. The reaction is normally carried out in the temperature range of 80°–250° C. Preferably the leaving group is iodo or bromo.

Compounds of the formulae (XV) and X$^7$CH$_2$D are reacted together in the presence of a base under similar reaction conditions to those described above for the reaction between compounds of the formulae (V) and (VI). Preferably X$^7$ is bromo. Compounds of the formulae (XV) and D—CHO are conveniently reacted together in an alcohol such as ethanol or isopropanol, in the presence of NaCNBH$_3$ and acetic acid or, alternatively, hydrogenated in the presence of palladium-on-carbon.

Compounds of the formula (XV) may be prepared by reducing the related nitro compound.

The ether-forming reaction between compounds of the formulae L$^1$—CH$_2$D and (XVI) is typically performed in an inert solvent such as acetone or DMF, in a temperature range of ambient to 60° C., in the presence of a mild base. Suitable values for L$^1$ include tosylate, mesylate, triflate and halo, for example chloro or bromo. When L$^1$ is bromo, the reaction may, for example, be performed in DMF, at ambient temperature in the presence of a base such as potassium carbonate. When L$^1$ is hydroxy, the Mitsunobu reaction may be used (O. Synthesis, 1981, 1). For example performing the reaction in tetrahydrofuran or toluene in the presence of diethyl azodicarboxylate and triphenylphosphine.

The compounds of the formula L$^1$—CH$_2$—D and (XVI) may alternatively be reacted together using a phase transfer system.

The compounds of the formula (XVII) and R$^4$X$^8$ may be reacted together in an aprotic solvent such as DMF in the presence of a base such as sodium carbonate or sodium hydride. Suitable values for X$^8$ are halo, tosylate, mesylate and triflate, in particular halo such as iodo.

Compounds of the formula (XVIII) are conveniently reduced with lithium aluminium hydride or a borane, under standard conditions known in the art. Compounds of the formula (XVIII) may be formed as shown in Scheme 1. The compound of the formula (VC) is hydrolysed with an aqueous acid or base or basic peroxide, for example aqueous hydrochloric acid, sodium hydroxide or hydrogen peroxide, in a temperature range of 0° to 100° C. Carboxylic acid (XVIIIA) may then be reacted with an amine of the formula $R^7$—B—$NHR^8$ to give the compound of the formula (XVIII) under conditions known in the art for the formation of amides. For examples see pages 972–976 of 'Larock— Comprehensive Organic Transformations'; VCH: New York, 1989:

Compounds of the formula (XIXa) are conveniently prepared by reacting together compounds of the formulae (XlXa1) and (XlXa2) under conditions known for the Wittig or Emmons-Horner reaction.

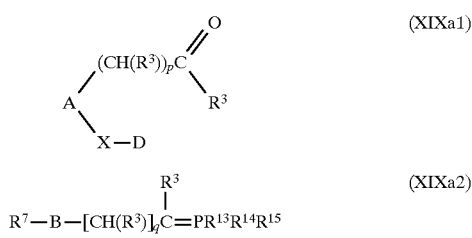

wherein p and q are independently 0 or 1, provided that p and q are not both 1. For example, under similar conditions to those described above for the reaction between compounds of the formulae (XIa1) and (XIa2).

The compounds of the formula (XIXa2) are rarely isolatable and usually prepared in situ by deprotonating a compound of the formula (XIXa3) (scheme 3). Deprotonation is usually carried out as described for the compounds of the formula (XIa3).

Compounds of the formula (XlXa3) may be prepared by reacting a compound of the formula (XlXa4) with a compound of the formula (XlXa5) (scheme 3). Suitable values for $X^{11}$ include halogen, such as chloro, bromo or iodo. Typically an inert solvent such as acetonitrile, diethyl ether, tetrahydrofuran or toluene is used and a temperature range of 50° C. to 120° C. The compounds of the formula (XIXa4) may be known or prepared from another compound of the formula (XIXa4) or a compound of the formula (XIXa6):

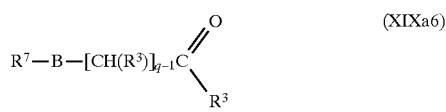

wherein B, $R^3$, $R^7$ and q are as hereinabove defined. For example the compound of the formula (XIXa6) may be reduced to a compound of the formula (XIXa4) wherein $X^{11}$ is hydroxy. A compound of the formula (XIXa4), wherein $X^{11}$ is hydroxy, may then be converted to a compound of the formula (XIXa4) wherein $X^{11}$ is bromo by, for example, bromonating with tetrabromomethane/triphenylphosphine or tribromophosphine.

Scheme 3

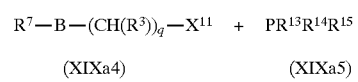

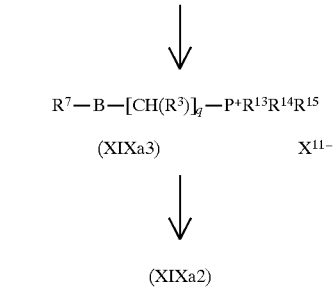

wherein B, $R^3$, $R^7$, $R^{13}$—$R^{15}$, p, q and $X^{11}$ are as hereinabove defined.

Alternatively compounds of the formula (XIXa) can be prepared by dehydrating a compound of the formula (XIXa7).

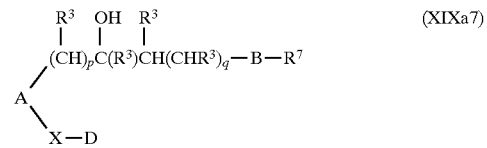

wherein A, B, D, X, p, q, $R^3$ and $R^7$ are as hereinabove defined. Dehydration is conveniently carried out using standard methods known in the art, for example, it elevated temperatures in the presence of sulphuric acid, phosphoric acid or aluminium oxide. Alternatively, the hydroxy group may be converted to a better leaving group such as tosylate which can then be converted to bromo. The alkene can then be formed by treatment with a strong base such as sodium hydride or LDA.

Compounds of the formula (XIXa7) can be prepared by reacting together compounds of the formula $R^7$—B—[CH($R^3$)]$_q$CH($R^3$)⁻ in the form of a zinc or Grignard reagent and (XIXa8).

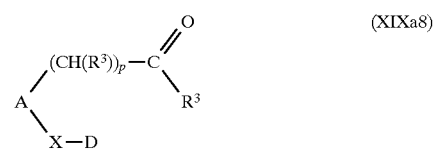

Standard conditions for the preparation of zinc or Grignard reagents are known in the art.

Compounds of the formula (XIXb) may be prepared by reacting a $R^7$—B—$X^{12}$ Cu(I) salt with a compound of the formula (XIXb1):

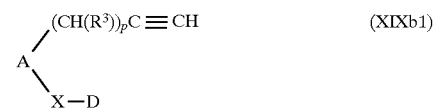

under conditions described above for the 'Heck reaction', wherein D, $R^3$ and A are as hereinabove defined and p is 0 or 1 and $X^{12}$ is a leaving group.

Compounds of the formula (XIXb 1) may be prepared by reacting together compounds of the formulae TMS—C≡CH or CH≡CC(Me)$_2$OH and (XIXb2):

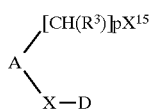
(XIXb2)

wherein A, D, X, R³, X¹⁵ and p are as hereinabove defined, under Heck conditions. For example, by performing the reaction in an inert solvent, such as dimethylformamide, tetrahydrofuran or NMP, in the presence of palladium (0), copper (I) in the form of a salt such as the halide or triflate, and a base such as triethylamine, tributylamine, 1,8-diazobicyclo[5.4.0]undec-7-ene (DBU) or potassium acetate.

Compounds of the formula (XX) are reduced by standard methods known in the art for the reduction of α,β-unsaturated ketones, without affecting ring B. For example, the double bond may be hydrogenated catalytically using Wilkinson's catalyst and then the ketone group reduced, if appropriate, by forming the tosyl hydrazone and reducing with sodium borohydride.

The compounds of the formula (XX) are conveniently prepared by reacting a compound of the formula (XXA) with a compound of the formula (XXB):

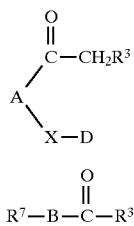
(XXA)

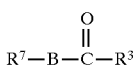
(XXB)

The reaction between the compounds of the formula (XXA) and (XXB) is conveniently carried out in the presence of a base, for example, lithium hydroxide or potassium tert-butoxide in an organic solvent such as alcohol, for example, methanol.

The reaction between the compounds of the formulae (XXI) and (XXII) is conveniently performed under standard conditions known in the art. Suitable leaving groups include halo, for example, chloro, bromo or iodo, and tosylate and mesylate.

In general the reaction is performed in an inert solvent such as hexane, tetrahydrofuran or ethyl ether, in a temperature range of –100° C. to ambient temperature, in the presence of a strong base such as butyl lithium, sec-butyl lithium, tert-butyl lithium, lithium diisopropylamide (LDA) or lithium hexamethyldisilylamide, preferably in the presence of a hindered base such as LDA or lithium hexamethyldisilylazide. For example wherein the leaving group is bromo, in in the presence of LDA at 30° C.

Compounds of the formula HP¹—B—R⁷ and (XXIII) are conveniently reacted together in the presence of a base in a dipolar aprotic solvent such as DMF. When the Mitsunobu reaction is used, no base is necessary. Otherwise the reaction is conveniently performed in the presence of a base. For example when P is sulphur, a suitable base is potassium carbonate and when P is oxygen, a suitable base is sodium hydride.

Suitable values for X¹³ include halo, tosylate, mesylate or hydroxy activated with triphenylphosphine/diethylazodicarboxylate or other Mitsunobu reagents.

The compound of the formula (XXIII) can be prepared from the related compound in which X¹³ is hydroxy. For example by reacting the hydroxy compound with tosyl or mesyl chloride in the presence of a base such as triethylamine.

The reaction between compounds of the formulae X¹⁴—B—R⁷ and (XXIV) is conveniently carried out in an inert polar aprotic solvent such as dimethylformamide or NMP in a temperature range of 80°–210° C.

Suitable values for X¹⁴ include halo and tosyl.

When P is sulphur, the compound of the formula (XXIV), can be prepared by reacting a compound of the formula (XXIII) with sodium sulphide in the presence of zinc/hydrochloric acid, triphenylphosphine/water or aqueous base in a temperature range of 20°–100° C.

The compounds of the formulae (XXIII), (XXIII) in which X¹³ is hydroxy and (XXIV) can be prepared using processes for the formation of the lower linking group —X— as described hereinabove, from appropriate starting materials.

The reaction between compounds of the formulae (XXV) and (VI) is conveniently carried out under mild conditions known for the Mitsunobu reaction (Mitsunobu, O. Synthesis 1981, 1), for example in the presence of di (C$_{1-4}$alkyl) azocarboxylate and triphenylphosphine or 1¹,1¹-(azodicarbonyl)dipiperidine and tributylphosphine (Tet. Lett. 34, 1993, 1639–1642) in an inert solvent such as toluene, benzene, tetrahydrofuran or diethylether, in particular toluene. Examples of removable activating groups are tert-butyloxycarbonyl and trifluoroacetyl.

Furthermore the alkoxycarbonyl groups can be removed by hydrolysis of the ester to leave the unprotected amino group and trifluoroacetyl groups reduced to 2,2,2-trifluoroethyl.

When R⁸ is alkoxycarbonyl and X¹ a leaving group such as tosylate, mesylate, chloro, bromo or iodo, the compounds of the formula (XXV) and (VI) can be reacted together to form a compound of the formula (I) or (III), in the presence of a strong base such as sodium hydride, potassium hydride, potassium tert-butoxide, lithium diisopropyl amine or LiN(SiMe$_3$)$_2$, in DMF or an etherial solvent such as diethyl ether or THF, in a temperature range of –78° C. to ambient temperature.

The compounds of the formula (XXV) may be prepared as shown in Scheme 4.

Scheme 4

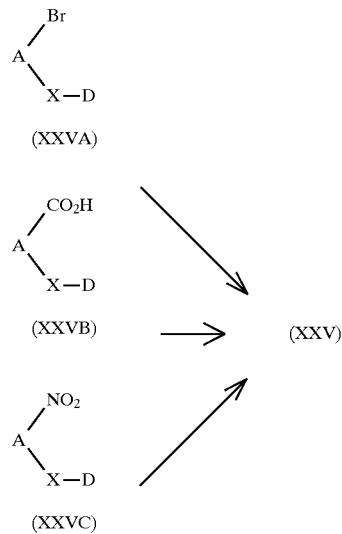

Compounds of the formula (XXVA) can be converted to a compound of the formula (XXV) by reacting (XXVA) with KCNO and tert-butanol in a polar aprotic solvent such as DMF or NMP, with a catalytic amount of pallaidum (0), in a temperature range of 80°–200° C.

Compounds of the formula (XXVB) are conveniently reacted with $(PhO)_2PON_3$ in a temperature range of 0°–20° C., followed by tert-butanol in a temperature range of 20°–100° C.

Compounds of the formula (XXVC) can be reduced to the amine with reagents such as zinc/hydrochloric acid, iron/acetic acid, tin (III) chloride, titanium (IV) chloride, or by catalytic hydrogenation. The amine can then be protected with tert-butoxycarbonyl to give a compound of the formula (XXV).

The compounds of the formulae (IVa1), (IVb1), (V), (VA), (VB), (VE), (IXC), (XIXa1), (XIXb2), (XIXa7), (XXA), (XXI), (XXIII), (XXIV), (XXVA), (XXVB) and (XXVC) can be prepared using processes for the formation of the lower linking group —X— as described hereinabove, from appropriate starting materials. Similarly, compounds of the formulae (XIa1), (XIa2), (XIII), (XIV), (XV) and the related nitro compound, (XIV) and the zinc or Gignard reagent used in the preparation of compounds of the formula (XII) can be prepared using processes for the formation of the —Z—B—$R^7$ group as described hereinabove, from appropriate starting materials.

The order in which the upper and lower links are constructed will depend upon the individual substitution patterns and the compatibility of functional groups with the reaction conditions.

The compounds of the formula (VII) may be prepared using processes a), b), d)—r) from the appropriate starting material wherein $R^7$ is replaced with $R^{10}$.

The compounds of the formula (VIII) or (XVII) may be prepared by using any one of processes a), b), c), e)—r) from the appropriate starting materials wherein $R^8$ is hydrogen.

The compounds of the formulae (VI) are generally known in the art or can be made by methods analogous to or similar to those used in the examples or those known in the art for related compounds.

It is also possible to synthesise certain intermediates and even protected compounds using primarly ring synthesis. Here, reference is made to the compendium 'The Chemistry of Heterocyclic Compounds' E. C. Taylor and A. Weissberger (published by John Wiley & Sons) and 'Comprehensive Heterocyclic Chemistry', A. R. Katritby and C. W. Rees (published by Pergamon Press).

Optional substituents may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (I) and (III) and intermediates in the preparation of compounds of the formulae (I) and (II), when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ether, a nitro group by nitration with concentrated nitric acid concentrated sulphuric acid and bromine by bromination with bromine or tetra(n-butyl)ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$—induced contractions of the ileum; ileum was immersed in oxygenated Krebs solution containing indomethacin (4 µg/ml) and atropine (1 µM) and which was maintained at 37° C.; the ileum was subject to a tension of 1 g; a control dose response curve for $PGE_2$—induced contraction of the ileum was obtained; test compound (dissolved in dimethylsulphoxide) was added to the Krebs solution and a dose response curve for the $PGE_2$—induced contraction of the ileum in the presence of the test compound was obtained; the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test (a): $pA_2 > 5.3$;

Test (b): $ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (I) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the formula (I), or an in-vivo hydrolysable ester or amide or pharnaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflamnmatory agents such as an inhibitor of the enzyme 5-lipoxygenase (such as those disclosed in European Patent Applications Nos. 0351194, 0375368, 0375404, 0375452, 037547, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, takykinin and calcitonin gene related peptides (CGRP), or an $alpha_2$-adrenoceptor agonist, a $GABA_B$ receptor agonist, a calcium channel blocker, a sodium channel blocker, a $CCK_B$ receptor antagonist, a neurokinin antagonist or an antagonist and modulator of the action of glutamate at the NMDA receptor may usefully also be present in a pharmaceutical composition of the invention.

The compounds of the present invention may also be administered in bone diseases such as osteoporosis with calcitonin and bisphosphonates.

The invention will now be illustrated in the following non-limiting Examples in which, unless otherwise stated:

(i) evaporations were carried out by rotary evaporations in vacuo and work-up procedures were carried out after removal or residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) intermediates were not generally fully characterised and purity was assessed by thin layer chromatographic, infra-red (IR) or NMR analysis;

(v) melting points are uncorrected and were determined usinga Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(vi) the following abbreviations have been used:
DMF N,N-dimethylformamide;
THF tetrahydrofuran
MPLC medium pressure liquid chromatography

EXAMPLE 1

4-[N-(2-Benzyloxy-5-bromobenzyl)aminomethyl]benzoic acid (adduct with acetic acid)

To a mixture of ethyl 4-[N-(2-benzyloxy-5-bromobenzyl)-aminomethyl]benzoate (1.4 g) in methanol (25 ml) was added 2N sodium hydroxide solution (7.7 ml). The mixture was heated at reflux for 30 minutes, left to stand for 2 hours at ambient temperature, the solvent evaporated and the residue mixed with water (20 ml). The mixture was acidified with acetic acid, the precipitate filtered off and crystallised form ethyl acetate to give the title compound (800 mg) mpt 209° C. The starting material was prepared as follows:

A mixture of 4-aminomethylbenzoic acid (25 g) and concentrated sulphtiric acid (25 ml) in ethanol (250 ml) was heated at reflux for 18 hours. The volume of solvent was reduced to a third by evaporation. The residue poured onto ice (500 g) and basified with concentrated aqueous ammonia. The product was extracted with ethyl acetate (3×200 ml) and the extracts dried and evaporated to give ethyl 4-aminomethylbenzoate.

2-Benzyloxy-5-bromobenzaldehyde and ethyl 4-aminomethylbenzoate were heated together at 100° C. for 1 hour. The mixture was cooled, dissolved in ethanol (100 ml) and sodium borohydride (1.3 g) was added. The mixture was stirred for 18 hours at ambient temperature, acidified with acetic acid and water (200 ml) was added. The mixture was extracted with diethyl ether (4×100 ml), the extracts washed with saturated aqueous $NaHCO_3$, dried ($MgSO_4$), filtered and evaporated to give ethyl 4-[N-(2-benzyloxy-5-bromobenzyl)aminomethyl]benzoate which was purified by chromatography on silica gel eluting with $CH_2Cl_2$ then 5% ethyl acetate/$CH_2Cl_2$ (yield 11.4 g).

EXAMPLE 2

4-[N-(2-benzyloxy-5-bromobenzyl)-N-ethylaminomethyl] benzoic acid

The title compound was prepared from ethyl 4-[N-(2-benzyloxy-5-bromobenzyl)-N-ethylaminomethyl]benzoate using a similar method to that described in Example 1.

The starting material was prepared as follows:

To a suspension of NaH (1.05 g, 50% dispersion in oil) in DMF (100 ml) at 0° C. was added a solution of ethyl 4-[N-(2-benzyloxy-5-bomobenzyl)aminomethyl]benzoate dropwise. The mixture was stirred at 0° C. for 1 hour, ethyl iodide (3.43 g) added and the mixture stirred at ambient temperature for 18 hours. The mixture was acidified with acetic acid, poured into water (300 ml) and extracted with ethyl acetate (3×100 ml). The combined extracts were washed with water (3×100 ml), dried and evaporated. The residue was purified by chromatography eluting with 4% ethyl acetate/$CH_2Cl_2$ to give ethyl 4-[N-(2-benzyloxy-5-bromobenzyl)-N-ethylaminomethyl]benzoate (yield 6.61 g).

EXAMPLE 3

4-[N-(5-Bromo-2-benzyloxybenzyl)-N-(4-tertbutoxycarbonylphenl)-aminomethyl]benzoic acid tert-Butyl 4-[N-(5-bromo-2-benzyloxybenzyl)-N-(4-methoxycarbonylbenzyl)amino]benzoate (from example 16) was dissolved in a solution of methanol (10 ml) and tetrahydrofuran (10 ml). To this solution was added aqueous 2N sodium hydroxide (3 ml) and the solution stirred at ambient temperature for 18 hours. The volume of the reaction mixture was reduced by evaporation to half the original volume, water (20 ml) was added and the mixture acidified with acetic acid. The resulting solid was filtered and dried under vacuum at 60° C. to give the title compound (12 g) m.p. 110° C.

EXAMPLE 4

4-[N-(5-Bromo-2-(phenethyl)benzyl)amino]benzoic acid
(A) Methyl 4-[N-(5-bromo-2-(phenethyl)benzyl)amino] benzoate (0.25 g) and 2N aqueous NaOH (5 ml) were heated at reflux in a mixture of methanol (5 ml) and THF (5 ml) for 2 hours. The organic solvents were evaporated, the residue acidified with 2N HCl and extracted with ethyl acetate. The extracts were washed with brine, dried ($MgSO_4$), filtered and evaporated. The residue was purified by crystallisation from diethyl ether and hexane to give the title compound (0.23 g; mpt 132°–134° C.).

The starting material was prepared as follows:
(B) A mixture of 5-bromo-2-hydroxybenzoic acid (50 g), methyl iodide (31.6 ml) and potassium carbonate (70 g) in DMF (200 ml) was stirred for 90 hours. The solvent was evaporated, the residue partitioned between diethyl ether and water, the organic layer was washed with brine, dried ($MgSO_4$), filtered and evaporated to give an oil (57.0 g).

The oil (57.0 g) and 2N NaOH (250 ml) in THF (150 ml) and methanol (50 ml) was heated at reflux for 1 hour. The solvent was evaporated, and the residue acidified with 2N HCl solution to give a solid which was isolated by filtration (50.68 g). The solid (50.68 g) was mixed with oxalyl chloride (20 ml), DMF (0.1 ml) and $CH_2Cl_2$ (300 ml) and stirred for 3 hours. The solvent was evaporated to give a yellow solid. The solid was dissolved in $CH_2Cl_2$ (150 ml) and added dropwise to a solution of 2-amino-2-methylpropan-1-ol (42 ml) in $CH_2Cl_2$ (100 ml) at 0° C. The mixture was stirred at ambient temperature for 18 hours, filtered and the filtrate washed sequentially with 2N HCl, water, saturated aqueous $NaHCO_3$ and brine, dried ($MgSO_4$), filtered and evaporated. The residue was purified by trituration from diethyl ether/hexane (1:1) to give N-(1-hydroxy-2-methylpropan-2-yl)-5-bromo-2-methoxybenzamide (46.34 g).

(C) Thionyl chloride (36.5 ml) was added dropwise to N-(1-hydroxy-2-methylpropan-2-yl)-5-bromo-2-methoxybenzamide (36.34 g). The resulting solution was stirred for 15 minutes and mixed with diethyl ether. The diethyl ether was decanted off and the resulting residue dissolved in 20% NaOH solution. The aqueous solution was extracted with diethyl ether. The extract was washed with brine, dried ($MgSO_4$) and evaporated to give 2-(5-bromo-2-methoxyphenyl)-4,4-dimethyl-4,5-dihydrooxazole (32.02 g).

(D) To a solution of 2-(5-bromo-2-methoxyphenyl)-4,4-dimethyl-4,5-dihydrooxazole (31.21 g) in THF (40 ml) was added $PhCH_2CH_2MgBr$ (0.22 mol) as a solution in diethyl ether (240 ml). The mixture was stirred for 18 hours, the solvents evaporated and the residue partitioned between ethyl acetate and saturated aqueous ammonium chloride. The organic layer was separated, evaporated and the resulting residue purified by MPLC eluting with dichloromethane to give 2-(5-bromo-2-(phenethyl)phenyl)-4,4-dimethyl-4,5-dihydrooxazole (40.56 g).

(E) To 2-(5-bromo-2-(phenethyl)phenyl)-4,4-dimethyl-4,5-dihydrooxazole (20 g) in diethyl ether (70 ml) at 0° C. was added DIBAL (168 ml, 1 Mol solution in $CH_2Cl_2$). The mixture was stirred at ambient temperature for 18 hours and cooled to 0° C. Aqueous 2N HCl was added to destroy excess DIBAL, the resulting solid was filtered off and suspended in a mixture of water and ethyl acetate. Triethylamine was added until the white solid was dissolved. The organic layer was separated, dried ($MgSO_4$) and evaporated to give 2-(N-(5-bromo-2-(phenethyl)benzyl)amino)-2-methylpropan-1-ol (14.21 g).

(F) A mixture of 2-(N-(5-bromo-2-(phenethyl)benzyl) amino)-2-methylpropan-1-ol (9.13 g), N-chlorosuccinimide (3.38 g) and dichloromethane (50 ml) was stirred for 4 hours. Aluminia (10 g) was added and the mixture stirred for 6 days, filtered and the solvent evaporated. The residue was dissolved in dichloromethane (200 ml) and alumina (60 g) added in 6 portions over 8 hours. The mixture was filtered, the filtrate evaporated and the residue purified by MPLC eluting with dichloromethane/hexane (1:1) to give 5-bromo-2-(phenethyl)benzaldehyde (3.54 g).

(G) 5-Bromo-2-(phenethyl)benzaldehyde (1.27 g) and methyl 4-aminobenzoate (0.66 g) were heated together at 110° C. for 30 minutes and for a further 30 minutes under vacuum. The mixture was dissolved in toluene, evaporated to dryness, dissolved in ethanol (15 ml). Sodium borohydride (0.33 g) was added, the mixture stirred for 18 hours, the solvent evaporated and the residue mixed with acetic acid and partitioned between saturated aqueous sodium hydrogen carbonate and ethyl acetate. The organic layer was washed with brine, dried (MgSO$_4$), filtered and evaporated. The resulting residue was purified by MPLC, eluting with dichloromethane, to give methyl 4-[N-(5-bromo-2-(phenethyl)benzyl)amino]benzoate (1.65 g).

EXAMPLE 5

4-[N-(2-(Phenethyl)benzyl)-N-ethylamino]benzoic acid
(A) 4-[N-(2-Phenethyl)benzyl)-N-ethylamino]benzoic acid was prepared from methyl 4-[N-(2-phenethyl)benzyl)-N-ethylamino]benzoate using a similar method to that of Example 4 paragraph (A) (mpt. 185°–186° C.).

The starting material was prepared as follows:
(B) A mixture of 2-phenethyl benzoic acid (11.3 g), oxalyl chloride (5.2 ml), DMF (0.2 ml) and dichloromethane (100 ml) was stirred for 1.5 hours. The solvent was evaporated, diglyme (75 ml) added and the mixture cooled to –70° C. Lithium tri-(tert-butoxy)aluminium hydride (100 ml, 0.5M solution in diglyme) was added dropwise over 45 minutes maintaining the reaction temperature below –60° C. The reaction was stirred at –70° C. for 1 hour and poured into a 2N HCl and ice mixture. The mixture was extracted with iso-hexane (3×100 ml). The extracts were washed with saturated aqueous sodium hydrogen carbonate, water and brine, dried (MgSO$_4$), filtered and evaporated. The residue was purfied by MPLC eluting with dichloromethane/iso-hexane (1:1) to give 2-(phenethyl)benzaldehyde (7.77 g).
(C) Methyl 4-[N-(2-(phenethyl)benzyl)amino]benzoate was prepared from 2-(phenethyl)benzaldehyde and methyl 4-aminobenzoate using a similar method to that of Example 4 paragraph (G).
(D) To a mixture of sodium hydride (0.69 g) in DMF (20 ml) was added dropwise a solution of methyl 4-[N-(2-phenethyl)benzyl)amino]-benzoate (5.41 g) in DMF (30 ml) at 0° C. The mixture was stirred for 30 minutes at 0° C., ethyl iodide (1.4 ml) was added and the mixture stirred at ambient temperature for 18 hours. The solvent was evaporated, the residue partitioned between ethyl acetate and water, the organic layer was washed with brine, dried (MgSO$_4$), filtered and evaporated.

The residue was purified by MPLC eluting with dichloromethane to give methyl 4- [N-(2-(phenethyl)benzyl)-N-ethylamino]benzoate (3.07 g).

EXAMPLE 6

N-Propyl-4-[N-ethyl-N-(2-(phenethyl)benzyl)amino]benzamide
  4-[N-(2-(Phenethyl)benzyl)-N-ethylamino]benzoic acid (1.5 g), oxalyl chloride (0.43 ml), DMF (0.1 ml) and CH$_2$Cl$_2$ (50 ml) were stirred together for 2 hours. The solvent was evaporated and the residue re-dissolved in dichloromethane (100 ml). This was added to a solution of propylamine (0.35 ml) in dichloromethane (10 ml) at 0° C. The resulting mixture was stirred for 2 hours at ambient temperature, filtered and the filtrate purified by MPLC, eluting with ethyl acetate to give a gum. The gum was purified by crystallisation from diethyl ether/iso-hexane to give N-propyl-4-[N-ethyl-N-(2-(phenethyl)benzyl)-amino]benzamide e (0.31 g) as a white solid, (mpt. 91°/93° C.).

EXAMPLE 7

The compounds in the table were prepared from the appropriate acids and amines by a similar method to that described in Example 6. Modifications are described in the footnotes.

TABLE 1

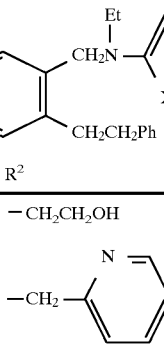

| Compound No. | R$^1$ | R$^2$ | X | mpt./°C. | Footnote |
|---|---|---|---|---|---|
| 1 | H | —CH$_2$CH$_2$OH | CH | gum | |
| 2 | H | 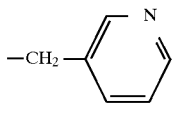 | CH | 54–56 | a |
| 3 | H | 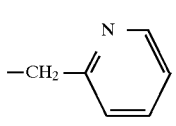 | CH | gum | a |
| 4 | Br | —CH$_2$CH$_2$OH | CH | 126–127 | |
| 5 | Br | 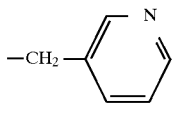 | CH | gum | a |
| 6 | H | —CH$_2$CH$_2$OH | N | gum | |
| 7 | H | —CH$_2$CH$_2$CH$_3$ | N | gum | |

Footnotes
a. Two equivalents of triethylamine were added with the amino.

EXAMPLE 8

4-[N-(5-Bromo-2-(phenethyl)benzyl)-N-ethylamino]benzoic acid
(A) The title compound was prepared from methyl 4-[N-(5-bromo-2-(phenethyl)benzyl)-N-ethylamino]benzoic acid using a similar method to that of Example 4 paragraph (A) (mpt 164°–165° C.).
(B) Methyl 4-[N-(5-bromo-2-(phenethyl)benzyl)-N-ethylamino]benzoic acid was prepared from methyl 4-[N-(5-bromo-2-(phenethyl)benzyl)amino]benzoate using a similar method to that described in Example 5 paragraph (D).

EXAMPLE 9

2-[N-Ethyl-N-(2-(phenethyl)benzyl)amino]pyridine-5-carboxylic acid (A) The title compound was prepared from methyl 2-[N-ethyl-N-(2-(phenethyl)benzyl)amino]pyridine-5-carboxylate using a similar method to that of Example 4 paragraph (A) (mpt 113°–116° C.).

The starting material was prepared as follows:
(B) 6-Chloronicotinic acid (100 g) and concentrated aqueous ammonia (500 ml) were heated in a bomb at 170° C. for 6 hours. The mixture was acidified with acetic acid and 2-amino-5-pyridinecarboxylic acid (78.69 g) filtered off.
(C) A mixture of 2-amino-5-pyridinecarboxylic acid, methanol (900 ml) and concentrated sulphuric acid (80 ml) was heated at reflux for 18 hours, some of the solvent (500 ml) was evaporated, the pH of the residue was adjusted to 8 with potassium carbonate and the residue was extracted with ethyl acetate (3×200 ml). The organic extracts were dried (MgSO$_4$), filtered and evaporated to give methyl 2-amino-5-pyridinecarboxylate (58.18 g).
(D) Methyl 2-[N-(2-(phenethyl)benzyl)amino]pyridine-5-carboxylate was prepared from methyl 2-amino-5- pyridinecarboxylate and 2-phenethylbenzoic acid by a procedure similar to that described in Example 4 paragraph (G), except that the imine intermediate, methyl 2-[N-(2-(phenethyl)benzylidene)amino]-5-pyridinecarboxylate, was formed by heating methyl 2-amino-5-pyridinecarboxylate and 2-phenethylbenzoic acid in a Dean & Starke apparatus in toluene for 18 hours.

(E) Methyl 2-[N-ethyl-N-(2-(phenethyl)benzyl)amino] pyridine-5-carboxylate was prepared from methyl 2-[N-(2-phenethyl)benzyl)amino] pyridine-5-carboxylate by a procedure similar to described in Example 5 paragraph (D).

EXAMPLE 10
2-[N-(5-Bromo-2-(phenethyl)benzyl)-N-ethylamino]-5-pyridinecarboxylic acid A) 2-[N-(5-bromo-2-(phenethyl)benzyl)-N-ethylamino]-5-pyridine carboxylic acid was prepared from methyl 2-[N-(5-bromo-2-(phenethyl) benzyl)-N-ethylamino]-5-pyridinecarboxylate using a similar method to that described in Example 4 paragraph (A).

The starting material was prepared as follows:
(B) Methyl 2-[N-(5-bromo-2-(phenethyl)benzyl)-N-ethylamino]-5-pyridinecarboxylate was prepared from 5-bromo-2-(phenethyl) benzaldehyde and methyl 2-amino-5-pyridinecarboxylate using a similar method to that described in Example 4 paragraph (G) followed by a similar method to that described in Example 5 paragraph (D).

EXAMPLE 11
2-[N-(2-(Benzyl)benzyl)-N-ethylamino]-5-pyridinecarboxylic acid

Methyl 2-[N-(2-(benzyl)benzyl)-N-ethylamino]-5-pyridinecarboxylate (0.9 g, 2.5 mmol) in THF (6 ml) and methanol (6 ml) were treated with 1N aqueous sodium hydroxide (7 ml), and stirred at ambient temperature overnight. The clear solution was evaporated to low bulk, treated with water and glacial acetic acid to pH4. The resultant white precipitate was stirred for 15 minutes, filtered, washed well with water, then sucked dry to yield the title product as a white solid (0.8 g, 92%).

MS: (M+H)$^+$347 (M.)$^+$346

The starting material was prepared as follows:
2-Benzylbenzyl alcohol (commercial) (1 g) was suspended in 48% aqueous hydrobromic acid (10 ml) and stirred vigorously for 20 hours. The resultant suspended solid was extracted twice with hexane and the extracts dried (MgSO$_4$) and evaporated to give 2-benzyl benzylbromide as yellow solid (1.3 g, 98%).

Sodium hydride (0.1 8 g, 50% in oil, 4.5 mmol) was prewashed with hexane and suspended in sieve-dried DMF (5 ml). To this was added (3.8 mmol) methyl 2-ethylaminopyridine-5-carboxylate (0.69 g). The mixture was stirred at −5° C. for 30 minutes, 2-benzyl benzyl bromide (1 g, 3.8 mmol) in DMF (2 ml) added over 3 minutes and the reaction left to stir at ambient temperature overnight. It was then poured into saturated aqueous ammonium chloride solution (20 ml) and extracted with ethyl acetate (×3). The combined extracts were washed with brine, dried and evaporated to give a brown gum (1.7 g). The gum was purified by MPLC on Merck silica (9385) to give methyl 2-[N-(2-(benzyl)benzyl)-N-ethylamino]-5-pyridinecarboxylate as a white solid (0.9 g, 66%).

EXAMPLE 12
6-(N-Ethyl-N-(2-phenoxybenzyl)amino)pyridazine-3-carboxylic acid 6-(N-Ethyl-N-(2-phenoxybenzylamino)pyridazine-3-carboxamide (0.60 g, 1.65 mmol) was dissolved in n-butanol (8.2 ml) and treated with sodium hydroxide (0.186 g, 4.65 mmol). The reaction was heated to reflux for 2 hours, cooled and evaporated at reduced pressure. The residue was diluted with water, acidified with HCl (1N) to pH 1 and extracted with ethyl acetate (3×). The organic layers were combined, dried (MgSO$_4$) and evaporated. The residue was purified by chromatography (CH$_2$Cl$_2$, MeOH, HOAc) to give the title product as a pale yellow solid (0.5 g, 86%).

mpt 70°–75° C.; MS(CI$^+$) : 350 (M+H)$^+$ NMR (200 MHz, DMSO-d$_6$) δ: 1.09 (t, 3H), 3.6 (q, partially obscured by H$_2$O), 4.85 (s,2H), 6.8–7.43 (m, 10H), 7.8 (d, 1H).

The starting material was prepared as follows:
Ethylamine (70% solution, 5.2 ml, 80 mmol) was diluted with water (5.2 ml). A solution of 2-bromomethylphenyl phenyl ether (5.0 g, 19.02 mmol) in THF (25 ml) was added dropwise and the reaction stirred at ambient temperature for 2 hours. The volatile components were removed at reduced pressure, aqueous sodium hydroxide (1N, 20 ml) was added and the aqueous solution extracted with dichloromethane (2×). The organic layers were dried (MgSO$_4$), evaporated and purified by chromatography (eluant: CH$_2$Cl$_2$/EtOAc/MeOH) to give N-ethyl-N-(2-(phenoxy)benzyl)amine as a yellow solid (2.2 g, 51%).

MS (EI$^+$): 226 (M$^+$); NMR (250 MHz, DMSO-d$_6$) δ: 1.0 (t,3H), 2.53 (g, partially obscured by DMSO), 3.7 (5, 2H), 6.88 (m, 3H), 7.05–7.4 (m, 5H), 7.53 (dd, 1H)

3-Chloro-pyridazine-6-carboxamide (1.53, 9.69 mmol), N-ethyl-N-(2-(phenoxy)benzyl)amine (2.2 g, 9.69 mmol) and di-isopropylethylamine (3.87 g, 30 mmol) in DMF (19 ml) was heated to 135° C. for 20 hours. The reaction was cooled to ambient temperature and allowed to stand for 48 hours. It was partitioned between ethyl acetate/H$_2$O, the aqueous layer extracted with ethyl acetate and the organic layers washed with water (4×), dried (MgSO$_4$) and evaporated. The residue was subjected to chromatography (eluant: ethyl acetate/hexane) to give 6-(N-ethyl-N-(2-phenoxybenzylamino)-pyridazine-3-carboxamide as a brown solid (1.53 g, 43%).

NMR (200 MHz, DMSO-d$_6$)δ: 1.14 (t, 3H), 3.68 (q, 2H), 4.89 (s, 2H), 6.85–7.48 (m, 11H), 7.8 (d, 1H), 8.05 (bs, 1H). MS (CI$^+$): 349 (MH)$^+$

EXAMPLE 13
2-(N-ethyl-N-(2-phenoxybenzyl)amino)pyridine-5-carboxylic acid

A solution of methyl 2-(N-ethyl-N-(2-phenoxybenzyl)-amino)pyridine-5-carboxylate (0.65 g, 1.74 mmol) in THF (3 ml) and methanol (3 ml) was treated with aqueous sodium hydroxide (1N, 4 ml). The reaction mixture was heated at reflux for 3 hours cooled to ambient and allowed to stand for 60 hours, then heated at reflux for 3 hours. The organic solvent was evaporated, the residue diluted with water and acidified (pH1) with HCl (conc.). The aqueous suspension was extracted with ethyl acetate, the organic phase was dried (MgSO$_4$) and evaporated and the solid was recrystallized from ethyl acetate/water and dried under reduced pressure to give the title product.

mpt 170.5°–172.0° C. MS (FAB$^+$): 349 (MH)$^+$ NMR (250 MHz, DMSO-d$_6$) δ: 1.1 (t, 3H), 3.6 (q, 2H), 4.8 (s, 2H), 6.6 (d, 1H), 6.9 (d, 1H), 6.98 (m, 2H), 7.13 (m, 3H), 7.26 (m, 1H), 7.38 (m, 2H), 7.88 (dd, 1H), 8.6 (d, 1H), 12.3 (bs, 1H).

The starting material was prepared as follows:
0-Cresol (4.28 g, 80 mmol), bromobenzene (6,36 g, 40 mmol) potassium carbonate (5.72 g, 41.45 mmol) and copper (I) iodide were combined in a round bottomed flask under argon. The flask was placed in an ultrasound bath for 30 minutes and then the reaction was heated to 140° C. for 16 hours. After cooling to ambient temperature, the reaction mixture was dissolved in dichloromethane and the solution decanted from the solid. The organic layer was washed with 1N NaOH (2x), water (2x), dried (MgSO$_4$) and evaporated to give 2-benzyl phenyl ether which was used without purification in the subsequent step (5.35 g, 73%).

NMR (200 MHz, DMSO-d$_6$) δ: 2.17 (s, 3H), 6.8–7.6 (m, 9H)

A solution of 2-benzyl phenyl ether (5.35 g, 29.1 mmol) in CCl$_4$ (70 ml) was treated with NBS (5.18 g, 29.1 mmo) and benzoyl peroxide (0.150 g, 0.6 mmol). The reaction was heated to reflux over a high intensity lamp for 3 hours. The reaction wash filtered and the solvent evaporated at reduced pressure to give 2-bromomethylphenyl phenyl ether which was used without purification in the subsequent step.

MS CI$^+$: 262 [M]$^+$ NMR (200 MHz, DMSO-d$_6$) δ: 4.7 (s, 2H), 6.8–7.8 (m, 9H)

A suspension of sodium hydride (1.26 g, 31.5 mmol) in DMF (25 ml) was treated with methyl 2-N-ethyl nicotinate (5.23 g, 29.1 mmol). The mixture was stirred at ambient temperature for 1 hour and then 2-bromomethylphenyl phenyl ether (29.1 mmol) was added. The reaction was stirred at ambient temperature for 18 hours and then the reaction mixture partitioned between ethyl acetate/water. The organic layer was washed well with water, dried (MgSO$_4$) and evaporated. The residue was purified by chromatography (ethyl acetate/hexane) to give methyl 2-(N-ethyl-N-(2-phenoxybenzyl)amino)pyridine-5-carboxylate as a pink solid (2.2 g, 20%).

MS FAB$^+$: 363 (MH)$^+$ NMR (200 MHz, DMSO-d6) δ: 1.1 (t, 3H), 3.6 (q, 2H), 3.77 (s, 3H), 4.80 (s, 2H), 6.64 (d, 1H), 6.8–7,5 (m, 9H), 7.9 (dd, 1H), 8.62 (d,1H)

EXAMPLE 14

6-(N-Ethyl-N-(2-(benzylamino)benzyl)amino)pyridazine-3-carboxylic acid 6-(N-Ethyl-N-(2-(benzylamino)benzyl)amino) pyridazine-3- carboxamide (0.49 g) in n-butanol was treated with sodium hydroxide pellets (140 mg) and heated at gentle reflux for 9 hours. The reaction was allowed to cool, was evaporated to dryness and the residue taken into water and acidified with acetic acid. The mixture was extracted with ethyl acetate (x2) and the extracts dried and evaporated to give a gum which was purified by MPLC to give the title compound as a brown foam (220 mg, 45%).

NMR (DMSO-d$_6$+CD$_3$ COOD) δ: 1.07–1.20 (t, 3H), 3.55–3.70 (q, 2H), 4.35 (s, 2H) 4.90 (s, 2H), 6.45–6.60 (m, 2H), 6.95–7.30 (m, 8H), 7.85–7.93 (m, 1H). MS: 363 (M+H)$^+$

The starting material was prepared as follows:

2-Nitrobenzylbromide (0.23 mol) in tetrahydrofuran (500 ml) was added to a stirred mixture (4.35M) of 70% aqueous ethylamine (350 ml) and water (350 ml) over a 20 minutes. The reaction stood at ambient temperature for 1 hour, was reduced to low volume, treated with ice/water to 800 ml and basified with an aqueous solution of sodium hydroxide (1 ON, 23 ml). It was extracted with ether (2x) and the combined extracts dried (MgSO$_4$) and evaporated to give N-ethyl-2-nitrobenzylamine as a yellow oil (44 g, 100%).

NMR (CDCl$_3$) δ: 1.03–1.13 (t, 3H), 2.57–2.63 (q, 2H), 3.98 (s, 2H), 7.30–7.37 (m, 1H) 7.45–7.6 (m, 2H), 7.85–7.9 (dd, 1H).

N-Ethyl-N-(2-nitrobenzyl)amine (4 g, 22 mmol) in ethanol (100 ml) was treated with 10% palladium-on-carbon (180 mg) and hydrogenated at N.T.P. for 2 hours. When uptake of hydrogen had ceased the reaction was filtered through Celite and evaporated to give N-ethyl-N-(2-aminobenzyl)amine (3.3 g, 100%).

NMR (CDCl$_3$) δ: 1.08–1.15 (t, 3H), 2.63–2.74 (q, 2H), 3.60 (br, 1H), 3.80 (s, 2H) 6.63–6.70 (m, 2H), 7.01–7.12 (m, 2H).

N-Ethyl-N-(2-aminobenzyl)amine (707 mg, 4.7 mmol) in DMF (11 ml) was treated with 6-chloropyridazin-3-amide (4.7 mmol) followed by diisopropylethylamine (15.4 mol) and the reaction stirred at 140° under argon for 24 hours. The reaction was evaporated in vacuo (cold-finger) and the residue partitioned between water and ethyl acetate. The combined organic extracts were dried and evaporated to give a brown gum. The gum was purified by medium pressure chromatography to give 6-(N-ethyl-N-(2-aminobenzyl) amino)-pyridazine-3-carboxamide (500 mg, 30%).

NMR (DMSO-d$_6$) δ: 1.08–1.15 (t, 3H), 3.55–3.70 (q, 2H), 4.69 (s, 2H), 5.0–5.3 (br, 2H), 6.49–7.03 (m, 5H), 7.79–7.84 (d, 1H), 7.45 (br, 1H), 8.09 (br, 1H).

6-(N-Ethyl-N-(2-aminobenzyl)amino)pyridazine-3-carboxamide (2.06 mmol) was part dissolved in methanol (12 ml) and treated with benzaldehyde (240 mg, 2.25 mmol) followed by NaBH$_3$CN (130 mg, 2.06 mmol). The reaction was stirred at ambient temperature for 9 days. It was then acidified to pH2, stirred for 10 minutes to destroy excess NaBH$_3$CN, basified with sodium hydroxide and extracted with ethyl acetate (x2). The combined extracts were dried and evaporated to give a pale brown gum (1.3 g) which was purified by MPLC to give 6-(N-ethyl-N-(2-(benzylamino) benzyl)amino)pyridazine-3-carboxamide as a white solid (0.49 g, 66%).

NMR (DMSO-d$_6$)δ: 1.05–1.20 (t, 3H), 3.55–3.70 (q, 2H), 4.33 (s, 2H), 4.80 (s, 2H), 6.05–6.25 (br, 1H), 6.47–6.50 (d, 1H), 6.87–7.32 (m, 9H), 7.80–7.85 (d, 1H), 7.42 (br, 1H), 7.98 (br, 1H). MS: 362 (M+H)$^+$

EXAMPLE 15

6-[N-(5-Bromo-2-benzylaminobenzyl)-N-ethylamino] pyridazine-3-carboxylic acid

A mixture of 6-[N-(5-bromo-2-benzylaminobenzyl)-N-ethylamino]pyridazine-3-carboxamide (700 mg, 1.59 mmol), sodium hydroxide pellets (200 mg, 5.0 mmol) and butanol was stirred at reflux for 3 hours. The mixture was cooled, diluted with water (100 ml) and washed with hexane (2x100 ml). The aqueous layer was acidified with formic acid and extracted with dichloromethane (2x200 ml). The combined organic extracts were dried over anhydrous magnesium sulphate and evaporated to give a white solid, which was triturated with ether and filtered to give the title compound (500 mg).

m.p. 176° C.-dec. NMR (200 MHz, DMSO-d$_6$) δ: 1.13 (t, J=7 Hz, 3H); 3.64 (q, J=7 Hz, 2H); 4.33 (d, J=5 Hz, 2H); 4.83 (s, 2H); 6.15 (broad t, J=5 Hz, 1H); 6.45 (d, J=8 Hz, 1H); 6.98–7.30 (m, 8H); 7.85 (d, J=8 Hz, 1H). MS (ESP$^+$)$^:$ 441/443 (M+H)$^+$(1xBr)

The starting material was prepared as follows:

Stannous chloride dihydrate (22.5 g, 0.1M) was added in one portion to .a stirred mixture of N-ethyl-5-bromo-2-nitrobenzylamine (8.5 g, 32.8 mmol) and 36% hydrochloric acid (20 ml, 0.22M) in ethanol (250 ml) at ambient temperature. There was an exothermic reaction (50° C.) and a yellow solution formed, which was stirred for 1 hour allowing it to cool. The solvent was evaporated at reduced pressure and the residue dissolved in ethanol (100 ml) and stirred while diluting with ether (200 ml) until crystallisation occurred. The yellow solid was filtered off and washed with ether to give N-ethyl-5-bromo-2-aminobenzylamine as a salt, from which the free base was isolated by stirring with 2N sodium hydroxide solution (150 ml) and extracting into ether. The organic layer was dried over anhydrous magnesium sulphate and evaporated to give an oil (4.2 g).

NMR (200 MHz, CDCl$_3$) δ: 1.10 (t, J=7 Hz, 3H); 2.64 (q, J=7 Hz, 2H); 3.75 (s, 2H); 6.50 (dd, J=8, 2 Hz, 1H); 7.1–7.2 (m, 2H). MS (CI$^+$): 228/230 M$^+$(1xBr)

A mixture of N-ethyl-5-bromo-2-aminobenzylamine (4.2 g, 18.3 mmol), 6-chloropyridazine-3-carboxamide (3.0 g, 19.0 mmol), ethyl di-isopropylamine (7.0 ml) and DMF (50 ml) was stirred at 140° C. under argon for 16 hours. The mixture was cooled, evaporated at reduced pressure, the residue was then partitioned between 1N sodium hydroxide solution (100 ml) and a mixture of ethyl acetate, dichloromethane and methanol (10:10:1, 500 ml). The organic layer was separated, dried over anhydrous magnesium sulphate and evaporated to give a yellow solid (6.0 g). Crystallisation from ethyl acetate (500 ml) gave 6-[N-(5-bromo-2-aminobenzyl)-N-ethylamino]pyridazine-3-carboxamide as yellow rosettes (118 g) m.p. 208°–210° C.

NMR (200 MHz, DMSO-$d_6$) δ: 1.13 (t, J=7 Jz, 3H); 3.62 (q, J=7 Hz, 2H); 4.68 (s, 2H); 5.33 (s, 2H); 6.63 (d, J=8 Hz, 1H); 6.9–7.15 (m, 3H); 7.45 (broad s, 1H); 7.85 (d, J=8 Hz, 1H); 8.10 (broad s, 1H). MS (CI$^{+)}$: 349/351 (M+H)$^+$(1×Br); Analysis: Calc % C 48.0, H 4.6, N 20.0;

Found % C 48.0, H4.6, N19.7

To a mixture of 6-[N-(5-bromo-2-aminobenzyl)-N-ethylamino]pyridazine-3-carboxamide (900 mg, 2.57 mmol), benzaldehyde (0.6 ml, 5.9 mmol) and methanol (50 ml) stirred at 50° C., was added portionwise sodium cyanoborohydride (400 mg, 6.36 mmol). The solution was stirred for 16 hours at 20° C., by which time the product crystallised. It was filtered off and washed with methanol (10 ml) to give 6-[N-(5-bromo-2-benzylaminobenlzyl-N-ethylamino]pyridazine-3-carboxamide (850 mg) m.p. 160°–162° C.

NMR (200 MHz, DMSO-$d_6$) δ: 1.12 (t, J=7 Hz, 3H); 3.60 (q, J=7 Hz, 2H); 4.33 (s, 2H); 4.80 (s, 2H); 6.43 (d, J=8 Hz, 1H); 7.00–7.25 (m, 8H); 7.45 (broad s, 1H); 7.35 (d, J=8 Hz, 1H); 8.0 (broad s, 1H). MS (ESP$^+$): 440/442 (M+H)$^+$(1×Br)

EXAMPLE 16

4-[N-(5-Bromo-2-benzyloxybenzyl)-N-(4-methoxycarbonylbenzyl)amino]benzoic acid tert-Butyl 4-[N-(5-bromo-2-benzyloxybenzyl)-N-(4-methoxycarbonylbenzyl)amino]benzoate (1.79 g) was suspended in formic acid (10 ml) and heated on a steam bath until a clear solution formed. The reaction mixture was cooled and stood at ambient temperature for 18 hours. The resulting solid was filtered and washed with formic acid (2×5 ml) and dried under vacuum at 60° C. to give the title product (1.4 g).

The starting material was prepared as follows:

5-Bromo-2-benzyloxybenzoic acid [International patent application, publication no. WO 96/03380] and tert-butyl-4-aminobenzoate were heated on a steam bath for 2 hours. Ethanol (50 ml) and tetrahydrofuran (50 ml) were added to the hot reaction mixture. The solution was allowed to cool and sodium borohydride (1.4 g) was added. The reaction mixture was then stirred at ambient temperature for 3 hours, poured into water (200 ml) and extracted with dichloromethane (4×100 ml). The combined extracts were dried over magnesium sulphate tert-butyl 4-[5-bromo-2-benzyloxybenzylamino]benzoate which was used without further purification (18 g).

tert-Butyl 4-[5-bromo-2-benzyloxybenzylamino]benzoate (16.9 g) and methyl-4-bromomethylbenzoate were dissolved in in dimethylformamide (30 ml) and potassium carbonate (18 g) added. The mixture was stirred at ambient temperature for 24 hours and then poured into water (300 ml). The reaction mixture was extracted with ether (4×100 ml). The combined ether extracts were washed with water (3×100 ml) and brine (1×100 ml), dried over magnesium sulphate and evaporated. The residue was purified by MPLC eluting with 1:1 dichloromethane/hexane to give tert-butyl 4-[N-(5-bromo-2-benzyloxybenzyl)-N-(4-methoxycarbonylbenzyl)amino]benzoate (3.6 g) m.p. 154°–155° C.

EXAMPLE 17

4-[N-(5-Bromo-2-benzyloxybenzyl)-N-(4-carboxybenzyl)amino]benzoic acid tert-Butyl 4-[N-(5-bromo-2-benzyloxybenzyl)-N-(4-carboxybenzyl)-amino]benzoate (example 3) (500 mg) was suspended in formic acid (2 ml) and heated on a steam bath until a clear solution was obtained. This solution was left at ambient temperature for 18 hours and the resulting solid filtered, washed with formic acid (2×1 ml) and dried under vacuum at 60° C. to give the title product (340 mg) m.p. 271° C.

EXAMPLE 18

4-[2-Benzyloxybenzylthio]benzoic acid

Sodium hydride (6.5 g, 50% dispersion in oil) in DMF (100 ml) was cooled (0° C., ice bath) and 4-thiobenzoic acid (10 g) was added. After stirring for 30 minutes at 0° C., 2-bromomethylphenyl benzyl ether (18.6 g) as a solution in DMF (100 ml) was added. The reaction was stirred at ambient temperature for 18 hours, cooled (ice bath), water was added, and the mixture acidified with acetic acid. The resulting solid was isolated by filtration and recrystallised from methanol to give 4-[2-benzyloxybenzylthio]benzoic acid (24 g) (mpt. 144° C.).

EXAMPLE 19

N-(3-Pyridylmethyl)-4-[2-benzyloxybenzylthio]benzamide

To a stirred mixture of 3-aminomethylpyridine (324 mg) and triethylamine (1.51 g) in dichloromethane (20 ml) at 0° C. was added 4-[2-benzyloxybenzylthio]benzoylchloride in $CH_2Cl_2$ (10 ml) (3 mmol). The mixture was allowed to warm to ambient temperature, washed with saturated aqueous $NaHCO_3$ (3×20 ml), dried ($MgSO_4$), filtered and evaporated. The residue was triturated with diethyl ether (20 ml) and crystallised from ethyl acetate to give N-(3-pyridylmethyl)-4-[2-benzyloxybenzylthio]benzamide (220 mg). (mpt. 108° C.).

The starting material was prepared as follows:

4-[2-benzyloxybenzylthio]benzoic acid (6.3 g) and oxalyl chloride (2.26 g) were stirred in dichloromethane (100 ml) for 18 hours. The solvent was evaporated to give 4-[2-benzyloxybenzylthio]benzoylchloride which was dissolved in dichloromethane.

EXAMPLE 20

The compounds in the following table were prepared from 4-[2-benzyloxybenzylthio]benzoylchloride and the appropriate amine using a similar method to that described in Example 19.

TABLE

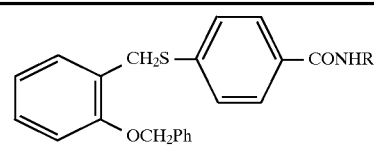

| Compound No. | R | mpt/°C. | Footnote |
|---|---|---|---|
| 1 | —CH$_2$CH$_2$OH | 112 | |
| 2 | —CH$_2$CH$_2$CH$_3$ | 98 | a |

TABLE-continued

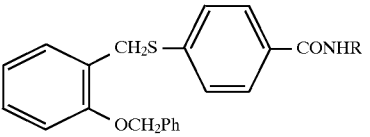

| Compound No. | R | mpt/°C. | Footnote |
|---|---|---|---|
| 3 | —CH₂CH₂—[triazole] | 156–158 | |

Footnote
a. Recrystallised from methanol.

EXAMPLE 21
4-(2-(Benzyloxy)benzyloxy)benzoic acid

Methyl 4-(2-(benzyloxy)benzyloxy)benzoate (1.01 g, 1.91 mmol) was dissolved in THF (20 ml) and methanol (7 ml). The solution was treated with NaOH (1N, 6 ml). The reaction was heated at reflux for 3 hours and then concentrated at reduced pressure. The pH was adjusted to pH1 with concentrated HCl and the solid filtered, washed with water and dried to give the title compound as a white solid (0.9 g, 98%).

mpt 176.8°–178.8° C.; Elemental Analysis for $C_{21}H_{18}O_4.0.2H_2O$; calc: 74.6%C 5.40%H; found: 74.8%C 5.40%H; NMR (200 MHz, DMSO-$d_6$) δ: 5.2 (s, 4H), 7.05 (m, 4H), 7.4 (m, 7H) 7.68 (d, 2H).

The starting material was prepared as follows:

A solution of methyl 4-hydroxybenzoate in DMF (5 ml) was treated with $K_2CO_3$ (2.76, 20 mmol) and 2-benzyloxy benzyl bromide (1.52 g, 10 mmol). The reaction was stirred at ambient temperature over night. The reaction mixture was partitioned between ethyl acetate and water and the organic phase was washed well with water dried (MgSO4) and evaporated. The crude material was purified by chromatography [EtOAc:hexane] to give methyl 4-(2-(benzyloxy)benzyloxy)benzoate as a white solid (3.06 g, 88%).

MS (FAB⁺): 349 [M+H]⁺; NMR (200 MHz, DMSO-$d_6$) δ: 3.81 (s, 3H), 5.2 (bs, 4H), 6.97 (m, 1H) 7.12 (m., 3H), 7.37 (m, 7H), 7.9 (m, 2H).

EXAMPLE 22
4-(1-(2-(Benzyloxy)phenyl)ethoxy)benzoic acid

Methyl 4-(1-(2-(benzyloxy)phenyl)ethoxy)benzoate (0.5 g, 1.4 mmol) was dissolved in THF (5 ml) and methanol (5 ml). The solution was treated with sodium hydroxide (1N, 6 ml) and the reaction heated at 60° for 3 hours. The solvent was removed at reduced pressure and the reaction mixture diluted with water and extracted with ethyl acetate. The aqueous phase was acidified (pH1) with concentrated HCl and extracted with ethyl acetate (3×). The organic phases were combined, dried (MgSO₄) and evaporated to give the title compound as a white solid (0.33 g, 68%).

mpt: 203°–204° C. Elemental Analysis for $C_{22}H_{20}O_4.0.3 H_2O$ calculated: C%:7.47 H%:5.9; found: C%:74.5 H%:5.8; MS (FAB⁻): 347 (M–H)⁻; NMR (200 MHz, DMSO-$d_6$) δ: 1.56 (d,3H) 5.24 (s,2H) 5.80 (q, 1H), 6.9 (m, 3H), 7.3 (m, 8H), 7.77 (d, 2H), 12.46 (bs, 1H).

The starting material was prepared as follows:

A solution of 2-benzyloxybenzaldehyde (4.24 g, 20 mmol) in THF (20 ml) was cooled to 020 C. and treated with a solution of methyl lithium (1.4M in diethyl ether 21.4 ml, 30 mmol). The reaction was stirred for 30 minutes at 0° C., then quenched with water and partitioned between ethyl acetate and water. The aqueous phase was extracted with ethyl acetate (2×) and the organic phases were combined, dried (MgSO₄) and evaporated to give 1-(2-benzyloxy) ethanol as a colourless oil (4.62 g, quantitative) which was used without purification in the subsequent step.

NMR (250 MHz, DMSO-$d_6$) δ: 1.3 (d, 3H), 4.93 (d, 1H) 5.08 (m, 3H), 6.96 (m, 2H), 7.17 (m, 1H) 7.4 (m, 6H)

A solution of 1-(2-benzyloxy)ethanol (4.56 g, 20 mmol) in THF (80 ml) was treated with methyl 4-hydroxybenzoate (3.34 g, 22 mmol), triphenylphosphine (5.76 g, 22 mmol) and diethyl azodicarboxylate (4.03 g, 22 mmol). The reaction was stirred at ambient temperature for 3½ hours. The solvent was evaporated at reduced pressure and the residue triturated with hexane and then filtered. The filtrate was evaporated, purified by chromatography (eluant:diethyl ether/hexane) to give methyl 4-(1-(2-(benzyloxy)phenyl) ethoxy)benzoate as a white solid (2.99 g, 41%) mp 90.8°–91.5° C.

MS (CI⁺) : 363 [M H⁺]; Elemental Analysis for $C_{23}H_{22}O_4$; calc, C%: 76.2%: H%: 6.12%; found:C%: 76.1: H%: 6.0; NMR (250 MHz, DMSO-$d_6$) δ: 1.57 (d, 3H), 3.78 (s, 3H), 5.25 (s, 2H), 5.82 (q, 1H), 6.9 (m, 3H), 7.35 (m, 8H), 7.8 (d, 2H).

The mixture was allowed to warm to ambient temperature, washed with saturated aqueous NaHCO₃ (3×20 ml), dried (MgSO₄), filtered and evaporated. The residue was triturated with diethyl ether (20 ml) and crystallised from ethyl acetate to give 4-(1-(2-(benzyloxy)phenyl) ethoxy)benzoic acid (220 mg). (mpt. 108° C.).

Methyl 4-(2-(benzyloxy)benzyloxy)benzoate (6.3 g) and oxalyl chloride (2.26 g) were stirred in dichloromethane (100 ml) for 18 hours. The solvent was evaporated to give 1-(2-benzyloxy)ethanol which was dissolved in dichloromethane.

EXAMPLE 23
4-(2-(phenethyl)benzyloxy)benzoic acid

The title compound was prepared from methyl 4-(2-(phenethyl)benzyloxy)benzoate using a similar method to that of example 21. m.p. 178°–180° C.

MS (FAB–): 331 (M–H); Elemental Analysis $C_{22}H_{20}O_3$; Calculated % C79.5, H6.06; Found % C79.4, H6.0;

NMR (200 MHz, DMSO-$d_6$) δ: 2.9 (m, 4H); 5.14 (s, 2H); 7.18 (m, 10H); 7.42 (d, 1H); 7.89 (m, 2H); 12.6 (bs, 1H).

The starting material was prepared as follows:

A solution of 2-(phenethyl)benzyl alcohol (0.424 g, 2 mmol) in toluene (25 ml) was treated with methyl 4-hydroxybenzoate (0.334 g, 2.2 mmol), triphenylphosphine (0.786 g, 3 mmol) and diethylazodicarboxylate (0.522 g, 0.47 ml, 3 mmol). The reaction was stirred at ambient temperature overnight and then diluted with ethyl acetate and washed with water and brine. The organic layer was dried over MgSO₄ and evaporated. The residue was purified by chromatography (eluant: ether/hexane) to give the methyl ester as a white solid (0.58 g, 84%).

NMR (200 MHz, DMSO-$d_6$) δ: 2.90 (m, 4H); 3.82 (s, 3H); 5.16 (s, 2H); 7.2 (m, 10H); 7.43 (bd, 1H); 7.93 (m, 2H).

EXAMPLE 24
4-[3-(2-Phenethylphenyl)propyl]benzoic acid (A) To a solution of methyl 4-[3-(2-phenethyl)phenyl) propyl]benzoate (6.25 g) in a mixture of THF (50 ml) and methanol (50 ml), was added 2N sodium hydroxide (42.5 ml). The mixture was stirred for 18 hours, the solvent volume reduced by half by evaporation and the residue poured into water and washed with diethyl ether. The aqueous layer was acidified with acetic acid and extracted with ethyl acetate (3×100 ml). The extracts were dried (MgSO₄), filtered and evaporated to give the title compound (5.24 g); mpt 97°–98° C.

The starting material was prepared as follows:

A mixture of 2-(phenethyl)benzoic acid (commercially available) (11.3 g), oxalyl chloride (5.2 ml), and DMF (2 drops) in dichloromethane (100 ml) was stirred for 1.5 hours. The resulting solution was evaporated and the residue dissolved in diglyme (75 ml) and cooled to –70° C. Li(O'Bu)₃H (100 ml of 0.5M solution in diglyme) was added dropwise over 45 minutes and the mixture stirred at –70° C. for 1 hour. The solution was poured into 2N aqueous hydrochloric acid and the mixture extracted with iso-hexane (3×100 ml). The combined extracts were washed with saturated aqueous sodium hydrogen carbonate, water and brine and dried (MgSO₄). The solvent was evaporated and the residue purified by medium pressure chromatography on silica gel eluting with a mixture of dichloromethane and iso-hexane (1:1) to give 2-(phenethyl)benzaldehyde acid as a colourless oil (7.77 g).

Lithium bis(trimethylsilyl)amide (56.7 ml, 1.0M solution in THF) was added to a mixture of 4-carboxyphenethyltriphenylphosphonium bromide (13.44 g, prepared from 4-(2-bromoethyl)benzoic acid by a standard method) in THF (100 ml), under argon and stirred for 1 hour. 2-Phenethylbenzaldehyde (5.75 g) in THF (50 ml) was added and the mixture stirred for 18 hours. The solvent was evaporated and the residue partitioned between water and diethyl ether. The aqueous layer was acidified with 2N HCl, and extracted with ethyl acetate (3×150 ml). The organic extracts were washed with brine, dried (MgSO₄), filtered and evaporated to give an oil (9.38 g). The oil (9.38 g) was dissolved in methanol (150 ml) and concentrated sulphuric acid heated at 100° C. for 12 hours, evaporated, mixed with water and extracted with diethyl ether (3×150 ml). The organic extracts were washed with saturated sodium hydrogen carbonate and water, dried (MgSO₄), filtered and evaporated. The residue was purified by MPLC eluting with dichloromethane: petroleum ether (1:1) to give an oil (6.96 g). The oil was dissolved in ethyl acetate (200 g) and added to 10% palladium on carbon (0.7 g). The resulting mixture was stirred under hydrogen for 18 hours, filtered through Celite and evaporated to give methyl 4-[3-(2-phenethyl)phenyl)propyl]benzoate as an oil (6.25 g).

EXAMPLE 25
N-(2-Hydroxyethyl)-4-[3-(2-(phenethyl)phenyl)propyl]benzamide (A) A mixture of 4-[3-(2-phenethylphenyl)propyl]benzoic acid (2.0 g), oxalyl chloride (0.56 ml) and DMF (0.1 ml) in dichloromethane (50 ml) was stirred for 4 hours. The solvent was evaporated to give an oil (2,2 g). To a stirred solution of ethanolamine (0.55 ml) in dichloromethane (50 ml) at 0° C. was added the oil (1.1 g) in dichloromethane (10 ml). The reaction was warmed to ambient temperature and stirred for 18 hours. The mixture was washed with water, dried (MgSO₄), filtered and evaporated to give a white solid. The solid was purified by crystallisation from ethyl acetate to give the title compound (811 mg); mpt 104°–106° C.

EXAMPLE 26
4-[2-(Phenethyl)phenethyl]benzoic acid

The title compound was prepared from methyl 4-[2-(phenethyl)phenethyl]benzoate using a similar method to that of Example 24 paragraph (A).

The starting material was prepared as follows:

Methyl 4-[2-(phenethyl)phenethyl]benzoate was prepared from 2-phenethylbenzaldehyde and 4-carboxybenzyltriphenylphosphonium bromide using a similar method to the described in Example 24 for the preparation of methyl 4-[3-(2-(phenethyl)phenyl)propyl]benzoate.

EXAMPLE 27

The compounds in the table were prepared from the acids 4-[3-(2-phenethylphenyl)propyl]benzoic acid or 4-[2-(phenethyl)phenethyl]benzoate and the appropriate amines by a similar method to that described in Example 25 with the modifications described in the footnotes.

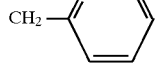

| Compound No. | n | R | mpt/°C. | Footnote |
|---|---|---|---|---|
| 1 | 3 | 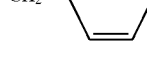 | 59–61 | a,b |
| 2 | 3 | CH₂CH₂CH₃ | 61–63 | c |
| 3 | 2 | CH₂CH₂OH | 72–75 | d |

Footnotes
a. 3 equivalents of triethylamine were added with the amine component.
b. Purified by crystallisation from hexane.
c. Purified by crystallisation from petroleum ether.
c. Purified by MPLC eluting with ethyl acetate.

EXAMPLE 28
4-[3-(2(Benzylamino)phenyl)propyl]benzoic acid (A) To a solution of ethyl 4-[3-(2-(benzylamino)phenyl)propyl]benzoate (1 g) in methanol (50 ml) was added 1N sodium hydroxide (13.4 ml). The mixture was stirred for 2 hours, heated at reflux for 10 minutes, the solvent was evaporated, the residue mixed with water (50 ml) and acidified to pH4 with 2N HCl. The mixture was extracted with ethyl acetate (3×20 ml) and the extracts washed with brine (2×20 ml), dried (MgSO₄), filtered and evaporated. The residue was triturated with petroleum ether (60–80) (25 ml) to give the title compound (0.55 g; 118° C.).

The starting material was prepared as follows:

(B) Ethyl 4-[3-(2-(benzylamino)phenyl)propyl]benzoate was prepared as follows: To a stirred suspension of LiOH H₂O (3.8 g) in ethanol (100 ml) was added a solution of 2-nitroacetophenone (15 g) and methyl 4-formylbenzoate (14.9 g) in ethanol (50 ml). The mixture was stirred for 20 minutes and the resulting solid filtered off and dried (22 g). A portion of this material (6.0 g) was dissolved in trifluoroacetic acid (100 ml), mixed with 10% palladium/carbon (1.0 g) and stirred vigorously under hydrogen for 24 hours. The solution was filtered through Celite, the solvent evaporated and the residue mixed with water. The mixture was neutralised with sodium hydrogen carbonate, and extracted with diethyl ether (3×50 ml). The extracts were dried (MgSO₄), filtered and evaporated. The residue was purified by flash chromatography with dichlorometliane and ethyl 4-[3-(2-aminophenyl)propyl]benzoate (3.21 g) and eluted with 10% ethyl acetate/dichloromethane. A mixture of ethyl 4-[3-(2-aminophenyl)propyl]benzoate (3.21 g) and benzaldehyde (1.21 g) was heated at 100° C. for 1 hour.

The mixture was dissolved in diethyl ether (25 ml), dried (MgSO₄), filtered and evaporated. The residue was dissolved in ethanol (100 ml) and sodium cyamoborohydride (0.5 g) was added. The mixture was stirred for 20 minutes, sodium cyanoborohydride (0.5 g) was added, the mixture was stirred for a further 1 hour, sodium cyanoborohydride (0.5 g) was added and the mixture was stirred for 18 hours. The mixture was poured into water (100 ml), acidified with acetic acid and extracted with diethyl ether (3×50 ml). The extracts were dried (MgSO$_4$), filtered and evaported. The residue was purified by flash chromatography eluting with 60% dichloromethane/petroleum ether to give ethyl 4-[3-(2-(benzylamino)phenyl)propyl]benzoate (3.8 g).

EXAMPLE 29

The compounds in the table were prepared from the corresponding ethyl esters by a similar method to that of Example 28 paragraph (A) with the modifications described in the footnotes.

The ester precursors were prepared as described in the footnotes.

| Compound No. | R | Mpt | Footnotes |
|---|---|---|---|
| 1 | CH$_2$Ph | 133 | a,b |
| 2 | Me | | a,c |

Footnotes
a. Purified by flash chromatography eluting with 1:1 ethyl acetate:dichloromethane.
b. A mixture of ethyl 4-[3-(2-(benzylamino)phenyl)propyl]benzoate (1.0 g), benzyl bromide (0.45 g) and 2,6-lutidine (280 mg) was stirred in DMF (5 ml) for 72 hours. The solvent was evaporated and the residue purified by flash chromatography eluting with 40% dichloromethane/petroleum ether to give ethyl 4-[3-(2-(N,N-dibenzylamino)phenyl)propyl]benzoate (1.4 g).
c. Ethyl 4-[3-(2-(N-benzyl-N-methylamino)phenyl)propyl]benzoate was prepared from ethyl 4-[3-(2-(benzylamino)phenyl)propyl]benzoate by a similar process to that described in footnote b but replacing benzyl bromide with methyl iodide.

EXAMPLE 30
4-[2-(2-(Phenethyl)-3-pyridyl)ethyl]benzoic

Methyl 4-[2-(2-(phenethyl)-3-pyridyl)ethyl]benzoate (0.46 g, 1.3 mmol) was dissolved in ethanol (10 ml) and treated with NaOH (1N, 2.66 ml). The reaction was stirred at ambient temperature for 60 hours. The reaction mixture was partially evaporated and neutralized with HCl. The precipitate was filtered, taken up in hot ethanol and filtered. The filtrate was evaporated, the residue was taken up in aqueous sodium hydroxide and acetic acid added which gave a precipitate.

The title product was recrystallised from ethanol/water (0.118 mg).

m.p. 152.1°–153.0° C.; MS (CI$^+$): 332 [M+H]$^+$

The starting material was prepared as follows:

A solution of sieve dried di-isopropylamine (3.24 g, 32 mM) in THF (20 ml) was cooled to –50° C. under argon and treated with n-butyl lithium (1.6M in hexrine, 19.2 ml). A suspension of 2-methyl nicotinic acid (2.0 g, 14.6 mmol) in THF (70 ml) was added slowly by syringe to the reaction mixture. A deep red/purple colour developed. The reaction was stirred for 0.75 hours allowing the temperature to rise to –40° C. The reaction was cooled to –60° C. A solution of benzaldehyde (1.86 g, 17.52 mmol) in THF (10 ml) was added dropwise keeping the temperature below –60° C. The colour of the reaction discharged to pale yellow within 15 minutes. The cooling bath was removed and the reaction was allowed to warm to 0° C. and was held at 0° C. for 18 hours. Water was added and the reaction acidified to pH2 with 1N HCl and extracted with EtOAc. The pH of the aqueous phase was adjusted to pH5 and re-extracted with EtOAc. The organic layers were combined, dried (56 mg) and evaporated. The resulting pale yellow oil was purified by chromatography eluting with (methanol/dichloromethane) to give 2-phenyl-8-oxopyrano[4,3-b]pyridine as a yellow oil (1.5 g) MS (CI$^+$): 226 [M+H]$^+$.

To a cooled solution (–70° C.) of 2-phenyl-8-oxopyranol [4,3-b]pyridine (1.09 g, 4.84 mmol) in dichloromethane (25 ml) was added DIBAL (1M in dichloromethane, 9 ml) keeping the temperature below –65° C. The reaction mixture was held at –70° C. for 4 hours. The reaction mixture was quenched by adding MeOH/dichloromethane (5 ml) (1/1), allowed to warm to ambient temperature and poured onto a slurry of SiO$_2$ and dichloromethane. The silica slurry was applied to the top of a chromatography column which was eluted with methanol/dichloromethane to give 2-phenyl-8-hydroxypyrano-[4,3-b]pyridine as a pale yellow solid (0.89 g, 81%). (It was used immediately in the following step) MS (FAB$^+$) 228 [M+H]$^+$.

4-Methoxycarbonylbenzyltriphenylphosphonium bromide (3.87 g 7.88 mmol) was suspended in THF (10 ml) and flushed with argon. Lithium bis(trimethylsilyl)amide (1M in THF, 8.66 ml) was added and the reaction stirred at ambient temperature for 0.75 hours (a deep orange colour developed). A suspension of 2-phenyl-8-hydroxypyrano-[4,3-b]pyridine (0.89 g, 3.94 mmol) in THF (10 ml) was added slowly. The reaction was stirred at ambient temperature overnight, then quenched by adding water, neutralised with hydrochloric acid, extracted with ethyl acetate, dried (MgSO$_4$) and evaporated. The crude material was purified by chromatography (eluting with EtOAc/hexane) to give rnethyl 4-[2-(2-(2-hydroxy-2-(phenyl)ethyl)-3-pyridyl) ethenyl]benzoate as the cis and trans isomers (0.95 g, 67%)

MS (CI+): 360 [M+H]$^+$.

Methyl 4-[2-(2-(2-hydroxy-2-(phenyl)ethyl)-3-pyridyl) ethenyl]benzoate (0.463 g, 1.29 mmol) was dissolved in ethanol (15 ml), acetic acid (3 drops) and 10% palladium on carbon (0.05 g).

The reaction was placed under a hydrogen atmosphere and stirred for 18 hours. The reaction was then filtered and evaporated to give methyl 4-[2-(2-(2-hydroxy-2-(phenyl) ethyl)-3-pyridyl)ethyl]benzoate as an oil (0.47 g)

MS(CI$^+$): 362 [M+H]$^+$.

Methyl 4-[2-(2-(2-hydroxy-2-(phenyl)ethyl)-3-pyridyl) ethyl]benzoate (0.47 g), 1.29 mmol) was cooled in an ice bath. Thionyl chloride (15 ml) was added and the reaction held at 0° C. for 1 hour. The reaction mixture was evaporated and azeotroped with toluene to give methyl 4-[2-(2-(2-chloro-2-(phenyl)ethyl)-3-pyridyl)ethyl]benzoate (0.549 g) which was used without further purification.

MS (CI$^+$): 380 [M+H]$^+$.

Methyl 4-[2-(2-(2-chloro-2-(phenyl)ethyl)-3-pyridyl) ethyl]benzoate (0.537 g, 1.29 mmol) was dissolved in ethanol (10 ml). The solution was treated with palladium on carbon (10% Pd, 0.1 g) and placed under a hydrogen atmosphere. The reaction was stirred at ambient temperature for 18 hours, then filtered and the solvent evaporated to give methyl 4-[2-(2-(phenethyl)-3-pyridyl)ethyl]benzoate (0.467 g), which was used without further purification.

MS (CI$^+$): 346 [M+H]$^+$

EXAMPLE 31
4-[2-(4-(Phenethyl)pyrid-3-yl)ethyl]benzoic acid
tert-Butyl 4-[2-(4-(phenethyl)pyrid-3-yl)ethyl]benzoate (0.36 g, 0.95 mmol) was dissolved in dichloromethane (5 ml) and treated with trifluoroacetic acid (0.5 ml). The reaction was stirred at ambient temperature for 5 hours, then partitioned between ethyl acetate and buffer (pH 6). The layers were separated and the aqueous layer extracted with ethyl acetate. The organic layers were combined, dried (MgSO$_4$) and evaporated to give the title product (0.168 g) as a salt with THF.

MS [CI$^+$]: 332 [M+H]$^+$; Elemental Analysis for C$_{22}$H$_{21}$NO$_2$.CF$_3$CO$_2$H: Calc: 63.5%C, 5.08%H, 3.1%N; Found: 63.5%C, 4.7%H, 2.8%N The starting material was prepared as follows:

A solution of di-isopropylamine (3.44 g, 34.1 mmol) was cooled to −78° C. and treated with n-butyl lithium 1.6M, 34.1 mmol). A solution of 3-bromopyridine (4.71 g, 30 mmol) in THF (5 ml) was added dropwise trying to keep the temperature below −70° C. The reaction was very exothermic, a solid precipitated and THF (2 ml) was added to improve stirring. The temperature rose to −45° C., after cooling to −60° C. and added remaining pyridine. DMF (2.49 g) in THF (15 ml) was added and the reaction stirred at −65° C. for 30 minutes. Water was added to quench the reaction and the reaction allowed to warm to ambient temperature. The reaction was partitioned between ethyl acetate/water and the aqueous layer extracted with ethyl acetate. The organic layers were combined, dried (MgSO$_4$) and evaporated and the residue was subjected to chromatography (eluting with diethyl ether/hexane) to give 3-bromo-4-pyridinecarbaldehyde (1.4 g, 76%).

MS(CI$^+$): 186 [M+H]$^+$.

Benzyldiethylphosphonate (1.94 g, 8.5 mmol) in THF (20 ml) was treated with lithium bis(trimethylsilyl)amide (8.6 ml, 1M). The reaction was stirred for 1.5 hours and a solution of 3-bromo-4-pyridinecarbaldehyde (1.4 g, 7.7 mmol) in THF (20 ml) added. The reaction was allowed to stand at ambient temperature for 18 hours, then partitioned between ethyl acetate/water. The organic layer was dried (MgSO$_4$) and evaporated and the residue purified by chromatography (eluting with diethyl ether/hexane to give 3-bromo-4-(2-phenylethenyl)pyridine (0.77 g, 39%)

MS(CI$^+$): 260 [M+H]$^+$.

3-Bromo-4-(2-phenylethenyl)pyridine (0.74 g, 2.9 mmol) was dissolved in DMF (1.4 ml). The solution was treated with tert-butyl 4-ethynylbenzoate (0.93 g 4.6 mmol), copper (III) iodide (0.023 g, 0.21mmol) and triethylamine (0.64 g, 6.3 mmol). The reaction mixture was degassed by bubbling through argon and the catalyst, bistriphenyl phosphinepalladium dichloride (0.03 g, 0.043 mmol), was added. The reaction was heated to 90°–100° C. for 3 hours and then partitioned between ethyl acetate and water. The organic layer was washed with water (3×), dried (MgSO$_4$) and evaporated. The residue was purified by chromatography (eluting with ethylacetate/hexane) to give tert-butyl 4-[2-(4-(2-phenylethenyl)-3-pyridyl)ethynyl]benzoate as a dark oil (0.36 g, 33%).

MS [CI$^+$]: 382 [M+H]$^+$ tert-Butyl 4-[2-(4-(2-phenylethenyl)-3-pyridyl)ethynyl] benzoate (0.360 g, 0.95 mmol) was dissolved in ethanol/ THF 1:1 (10 ml) and treated with palladium on carbon (10%, 0.13 g). The reaction was placed under a hydrogen atmosphere and stirred at ambient temperature for 6 hours. The reaction was then filtered and evaporated to give tert-butyl 4-[2-(4-phenethyl-3-pyridyl)ethyl]benzoate (0.36 g).

MS(CI$^+$): 388 [M+H]$^+$.

EXAMPLE 32
4-[3-(2-(phenylthio)phenyl)propyl]benzoic acid

The title compound was prepared from the corresponding ethyl ester using a similar method to that of example 24 (A) except using ethanol in place of methanol. The title product was crystallised from hexane/ether (9:1) to give white platelets m.p. 90°–91° C.

NMR (200 MHz, DMSO-d$_6$) δ 1.86 (m, 2H); 2.6–2.9 (m, 4H); 7.1–7.4 (m, 11H); 7.85 (d, J=8 Hz, 2H); 12.7 (broad s, 1H). MS (FAB$^-$): 347 (M−H)$^-$; Elemental Analysis: Calc % C 75.8: H, 5.8; S, 9.2; Found % C 75.9; H, 5.8; S, 9.6

The starting material was prepared as follows:

To a solution of 4-carboxyphenethyl triphenylphosphonium bromide (11.2 g, 22.8 mmol) in THF (200 ml) under argon, was added a 1M solution of lithium hexamethyldisilazide (50 ml) in THF at 20° C., giving a deep red colour. After stirring for 30 minutes, the reaction was treated with a solution of 2-bromobenzaldehyde (4.0 g, 21.6 mmol) in THF (15 ml) and stirred for a further 30 minutes at 20° C. The solution was poured onto a stirred mixture of water (100 ml) and ether (100 ml). The layers were separated and the aqueous portion washed again with ether (100 ml), acidified with 1N HCl and extracted with ether (100 ml). The ether extracts were dried over anhydrous magnesium sulphate and "flashed" through a pad of silica to remove impurities, rinsing with further portions of ether. The filtrates were evaporated to give 4-[3-(2-bromophenyl)prop-2-en-1-yl] benzoic acid (6.1 g) as a yellow gum, which slowly solidified.

To a solution of 4-[3-(2-bromophenyl)prop-2-en-1-yl] benzoic acid (5.8 g) in ethyl acetate (100 ml) was added 5% palladium-barium sulphate catalyst (1.4 g) and the stirred mixture sealed in a hydrogen atmosphere for 50 hours at S.T.P. The mixture was filtered and evaporated at reduced pressure to give a solid (5.0 g) which was crystallised from 5% aqueous methanol (150 ml) to give 4-[3-(2-bromophenyl)propyl]benzoic acid (4.0 g) as white rhombs.

NMR (200 MHz, DMSO-d$_6$) δ: 1.90 (m, 2H); 2.70 (m, 4H); 7.15 (m, 1H); 7.32 (m, 4H); 7.57 (d, J=7 Hz, 1H); 7.87 (d, J=8 Hz, 2H). MS (CI$^+$): 319/321 (M+H)$^+$(1×Br) Analysis: Calc% C 60.2; H, 4.7; Br 25.0; Found% C 60.1; H, 4.7; B 24.7

To a solution of 4-[3-(2-bromophenyl)propyl]benzoic acid (2.0 g) in a mixture of chloroform (50 ml) and ethanol (50 ml) was added dropwise, with stirring, concentrated sulphuric acid (98% w/v, 5.0 ml) and the resulting solution allowed to stand for 40 hours at 20° C. The solution was poured onto a stirred mixture of chloroform (100 ml) and saturated sodium bicarbonate. The organic layer was separated, dried over anhydrous magnesium sulphate and evaporated to give ethyl 4-[3-(2-bromophenyl)propyl) benzoate (2.3 g).

To a solution of ethyl 4-[3-(2-bromophenyl)propyl) benzoate (1.0 g, 2.9 mmol) in NMP (10 ml), sealed and stirred under argon, was added diphenyl disulphide (1.5 mmol) and activated copper powder (0.2 g). The mixture was heated at 180° C. for 16 hours, cooled to 20° C. and poured into a mixture of ether (100 ml), water (100 ml) and ethylene diamine (3.0 ml). The organic layer was separated, dried over anhydrous magnesium sulphate and "flashed" through a pad of silica, rinsing with ether. The filtrates were evaporated to give ethyl 4-[3-(2-(phenylthio)phenyl)propyl] benzoate as an oil (1.0 g).

NMR (200 Mhz, DMSO-d$_6$) δ: 1.32 (t, J=7 Hz, 3H); 1.83 (m, 2H); 2.6–2.8 (m, 4H (q, J=7 Hz, 2H); 7.1–7.4 (m, 11H); 7.86 (d, J=8 Hz, 2H). MS (CI$^+$): 376 M$^+$

EXAMPLE 33
2-Hydroxy-4-[(2-phenethyl)phenethyl]benzoic acid

A solution of methyl 2-hydroxy-4-[2-(phenethyl) phenethyl]benzoate (0.25 g) in THF (5 ml) and methanol (5 ml) containing aqueous 2N sodium hydroxide (5 ml) was heated under reflux for 2 hours. The reaction mixture was evaporated to small volume and acidified with aqueous 2N hydrochloric acid. The mixture was extracted three times with ethyl acetate (25 ml each time) and the combined extracts were washed with brine and dried over anhydrous magnesium sulphate. The solid obtained on removal of the solvent was crystallised from a mixture of diethyl ether and hexane to give 2-hydroxy-4-[(2-phenethyl)phenethyl] benzoic acid (0.2 g), m.p. 134°–7° C.

The starting material was prepared as follows:
(A) Oxalyl chloride (9.1 ml) was added to a suspension of 2-bibenzylcarboxylic acid (20 g) in dichloromethane (200 ml) followed by 0.1 ml of DMF. The mixture was stirred for 15 hours and evaporated to dryness. The residue was dissolved in diglyme (150 ml) and cooled to –70° C. under argon. Lithium tri-t-butoxyaluminohydride (177 ml of a 0.5M solution in diglyme) was added dropwise such that the temperature of the reaction mixture did not exceed –65° C. The reaction mixture was stirred for a further 2 hours at –70° C. and then poured onto ice. The slurry obtained was acidified (HCl) and extracted with diethyl ether (3×75 ml). The combined ether extracts were washed with brine and dried (MgSO$_4$). The solvent was removed and the residue dissolved in petroleum ether (BP 60°–80° C.) and washed once with aqueous saturated sodium bicarbonate, five times with water and twice with brine then dried. Removal of the solvent gave an oil which was purified by chromatography on silica, eluting with dichloromethane-hexane (1:1 v/v), to give 2-(phenethyl)benzaldehyde, (4.83 g).
(B) To a suspension of (3-acetoxy-4-methoxycarbonyl) benzltriphenyl phosphonium bromide (13.7 g) in THF (40 ml) under argon was added dropwise over 30 minutes a 1M solution of lithium bis (trimethylsilyl) amide (52.35 ml) in THF. The mixture was stirred for 30 minutes, cooled to 0° C. and 2-(phenethyl)benzaldehyde (4.83 g) dissolved in THF (20 ml) was added dropwise over 30 minutes. The reaction mixture was allowed to warm to ambient temperature and was stirred for a further 15 hours, then poured into water, acidified with hydrochloric acid and the mixture was extracted with ethyl acetate (3×50 ml). The combined ethyl acetate extracts were washed with aqueous saturated sodium bicarbonate solution and brine and dried (MgSO$_4$). Removal of the solvent gave an oil which was subjected to chromatography on silica, eluting with a mixture of dichloromethane and hexane (1:1 v/v) to give trans methyl 2-hydroxy-4-[2-(2-(phenethyl)phenyl)ethenyl]benzoate (2.0 g).

A solution of methyl 2-hydroxy-4-[2-(2-(phenethyl) phenyl)ethenyl]benzoate [0.98 g] in ethanol (10 ml) and THF (10 ml) containing 10% palladium on carbon was stirred under an atmosphere of hydrogen (balloon) for 14 hours. The catalyst was removed by filtration and the filtrate evaporated to dryness to give methyl 2-hydroxy 4-[2-(2-phenethyl)phenyl]benzoate as a gum.

EXAMPLE 34
4-[3-(2-benzylphenyl)propyl]benzoic acid

A solution of 4-[3-(2-benzylphenyl)prop-1-enyl]benzoic acid (6.43 g) in THF (50 ml) containing 10% palladium on carbon (1 g) was stirred under an atmosphere of hydrogen (balloon) for 15 hours. The catalyst was removed by filtration and the residue obtained on removal of the solvent was purified by chromatography on silica. eluting with 5% methanol in dichloromethane, to give 4-[3-(2-benzylphenyl) propyl]benzoic acid, m.p. 135°–6° C.

4-[3-(2-Benzylphenyl)prop-1-enyl]benzoic acid was prepared by reaction of 2-benzylbenzaldehyde with 4-carboxyphenethyltriphenylphosphonium bromide using a similar method to that of example 33(B) to give a gum. [2-Benzylbenzaldehyde (an oil) was obtained from 2-benzylbenzoic acid using a similar method to that of example 33(A)].

EXAMPLE 35
4-[N-(2-Benzyloxyphenyl)aminomethyl]benzoic acid
(A) A mixture of methyl 4-[N-(2-benzyloxyphenyl) aminomethyl]-benzoate (2 g), 2N sodium hydroxide solution (14.4 ml), methanol (10 ml) and THF (10 ml) was heated at reflux for 30 minutes. Half the solvent was evaporated and the mixture acidified with acetic acid. The resulting solid was filtered, dried and re-crystallised from methanol (yield 1.1 g, mpt 163° C.).

The starting material was prepared as follows:
(B) 2-Nitrophenol (50 g), benzyl bromide (61.5 g) and potassium carbonate (99.3 g) were stirred in acetone for 72 hours. The mixture was filtered and the solvent evaporated to give a solid (86.1 g), the solid was mixed with ferric chloride (5 g) and water (200 ml) in methanol (200 ml) and heated at 700° C. Iron (69.4 g) was added in portions over 1hour. The mixture was heated at 80° C. for 1.5 hours, cooled and mixed with diethyl ether (500 ml). The mixture was filtered through Celite, washed with 2N NaOH (3×100 ml) and the organic layer separated, dried (MgSO$_4$), filtered and evaporated to give 2-benzyloxybenzamine (68.7 g).

2-Benzyloxybenzamine (10 g) and methyl 4-formylbenzoate (8.2 g) were heated at 100° C. for 3 hours, the mixture cooled to ambient temperatrue dissolved in ethanol (200 ml) and sodium borohydride (1.85 g) added. The mixture was stirred for 18 hours, the solvent volume reduced by half by evaporation, poured into water (200 ml) and acidified with acetic acid. The mixture was extracted with dichloromethane (3×100 ml), the extracts washed with saturated aqueous NaHCO$_3$ dried (MgSO$_4$) and evaporated. The residue was purified by chromatography eluting with 80% CH$_2$Cl$_2$/hexane to give methyl 4-[N-(2-benzyloxyphenyl)aminomethyl]benzoate (14 g).

EXAMPLE 36
4-[N-(2-Benzyloxyphenyl)-N-ethylaminomethyl]benzoic acid
(A) The title compound was prepared from methyl 4-[N-(2-benzyloxyphenyl)-N-ethylaminomethyl]benzoate (12.5 g) by a similar method to that described in Example 35. (yield 4.2 g).

The starting material was prepared as follows:
(B) To a suspension of NaH (1.38 g, 50% dispersion in oil) in DMF (50 ml) at 0° C. was added a solution of methyl 4-[N-(2-benzyloxyphenyl)aminomethyl] benzoate (10 g) in DMF (100 ml).

The mixture was stirred at 100° C. for 30 minutes, then ethyl iodide was added (4.5 g) and the mixture stirred at ambient temperature for 18 hours. The solvent was evaporated, the 20 residue dissolved in ethyl acetate (200 ml) and washed with water (2×50 ml) and brine, dried (MgSO$_4$) and evaporated to give methyl 4-[N-(2-benzyloxyphenyl)-N-ethylaminomethyl]benzoate (12.5 g).

EXAMPLE 37
4-[N-(2-Benzyloxy-5-bromophenyl)aminomethyl]benzoic acid
(A) The title compound (mpt 216°–217° C.) was prepared using a similar process to that described in Example 35 but from 4-bromo-2-nitrophenol.

EXAMPLE 38
4-[N-(2-Benzyloxy-5-bromophenyl)-N-ethylaminomethyl] benzoic acid (A) The title compound (mpt 94.5°–95.0° C.) was prepared by a similar process to that described in Example 36 from methyl 4-[N-(2-benzyloxy-5-bromophenyl)-N-ethylaminomethyl]benzoate.

EXAMPLE 39

4-[1-(N-(2-Benzyloxy-5-bromophenyl)-amino)ethyl]benzoic acid (A) The title compound (mpt 186.5°–187.0° C.) was prepraed from ethyl 4-[1-(N-(2-benzyloxy-5-bromophenyl)amino)ethyl]benzoate using a similar process to that of Example 35(A). The product was purified by crystallisation from ethyl acetate/hexane.

The starting material was prepared as follows:

(B) A mixture of 2-benzyloxy-5-bromobenzamine (2.0 g) and methyl 4-acetylbenzoate (1.28 g) was heated at 150° C. for 3.5 hours. The reaction mixture was purified by MPLC eluting with 1:1 $CH_2Cl_2$: hexane to give a solid (0.4 g). The material was dissolved in TFA (7 ml) and cooled to 0° C. $BH_3$.THF (1.77 ml; 1M solution in THF) was added dropwise. The reaction was quenched with water (1 ml) and the pH adjusted to about 9 with 2N NaOH solution. The mixture was extracted with ethyl acetate (2×50 ml), the extracts washed with brine, dried ($MgSO_4$), filtered and evaporated. The residue was purified by MPLC eluting with $CH_2Cl_2$: hexane (1:1) to give ethyl 4-[1-(N-(2-benzyloxy-5-bromophenyl)amino)ethyl]benzoate.

EXAMPLE 40

4-[1-(N-(2-Benzyloxy-4-bromophenyl)-N-methylamino)ethyl]benzoic acid (A) The title compound (mpt 181.5°–182° C.) was prepared from ethyl 4[1-(N-(2-benzyloxy-4-bromophenyl)-N-methylamino)ethyl]benzoate by a similar process to that of Example 35(A).

(B) The starting material was prepared from ethyl 4-[1-(N-(2-benyzloxy-5-bromophenyl)amino)ethyl]benzoate using a process similar to that of Example 36(A), except using methyl iodide in place of ethyl iodide. The product, ethyl4-[1 -(N-(2-benzyloxy-4-bromophenyl) N-methylamino)ethyl]benzoate, was purified by MPLC eluting with dichloromethane.

EXAMPLE 41

2-[N-(2-Benzyloxy-5-bromophenethyl)-N-ethylamino]-5-pyridinecarboxylic acid (A) tert-Butyl 2-[N-(2-benzyloxy-5-bromophenethyl)-N-ethylamino]-5-pyridinecarboxylate (800 mg) and trifluoroacetic acid (20 ml) in dichloromethane (20 ml) was heated at reflux for 30 minutes. The solvent was evaporated and the residue crystallised from a mixture of dichloromethane and diethyl ether (1:2) to give the title compound (600 mg) mpt 214° C. (decomp).

The starting material was prepared as follows:

(B) A mixture of 2-bromomethyl-4-bromophenyl benzyl ether (0.28 moles) and NaCN (16 g) in DMF (200 ml) was stirred at ambient temperature for 16 hours, then heated at 100° C. for 5 hours. A further 2 g of NaCN was added and the reaction heated for 5 hours at 100° C. The mixture was diluted with water (200 ml) and stirred (1 hour). The resulting solid was filtered off and recrystallised from methanol to give 4-bromo-2-cyanomethylphenyl benzyl ether (48 g) mpt. 75°–76° C.

(C) To a mixture of $NaBH_4$ (6.0 g) in THF (100 ml) was added dropwise trifluoroacetic acid (18 ml) at 0° C. (ice bath). 4-Bromo-2-cyanomethylphenyl benzyl ether (10 g) was added and the mixture stirred at ambient temperature for 18 hours. The reaction was quenched with water (100 ml), the pH adjusted to 13 with 2N aqueous NaOH solution, and extracted with diethyl ether. The diethyl ether extracts were dried ($MgSO_4$) and evaporated to give 2-(2-aminoethyl)-4-bromophenyl benzyl ether (11.0 g) as a yellow gum.

(D) A mixture of 2-(2-aminoethyl)-4-bromophenyl benzyl ether (3 g), tert-butyl 2-chloro-5-pyridinecarboxylate (2.1 g) (prepared from the acid by standard procedures), and potassium carbonate (1.4 g) in N-methylpyrrolidone (20 ml) was heated at 120° C. for 16 hours. To the reaction mixture was added diethyl ether (200 ml) and water (200 ml), the layers separated, the organic layer washed with water, dried ($MgSO_4$), filtered and evaporated. The residue was purified by flash chromatography on silica gel eluting with dichloromethane/ethyl acetate mixtures (100:0, 95:5) to give tert-butyl 2-[N-(2-benzyloxy-5-bromophenethyl)amino]-5-pyridinecarboxy late (1.0 g).

(E) A mixture of tert-butyl2-[N-(2-benzyloxy-5-bromophenethyl)-amino]-5-pyridinecarboxylate (850 mg), and sodium hydride (101 mg, 50% dispersion in oil) in DMF (20 ml) was stirred for 15 minutes then iodoethane (150 ml) was added and the mixture stirred for 2 hours. The mixture was diluted with diethyl ether (50 ml) washed with water, dried ($MgSO_4$), filtered through silica gel, evaporated and the residue re-dissolved in dichloromethane and evaporated to give tert-butyl 2-[N-(2-benzyloxy-5-bromophenethyl)-N-ethylamino]-5-pyridine carboxylate (800 mg).

EXAMPLE 42

The compounds listed in the table were prepared from the appropriate ester compounds using a similar method to that described in Example 41, paragraph A.

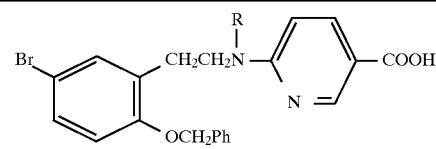

| Compound No. | R | adducts | Footnote |
|---|---|---|---|
| 1 | H | $CF_3CO_2H$ | a |
| 2 | Me | $CF_3CO_2H$ | a,b |
| 3 | —$CH_2CH=CH_2$ | $CF_3CO_2H$ | c,d |

Footnotes
a. Crystallised from diethyl ether.
b. tert-Butyl 2-[N-(2-benzyloxy-5-bromophenethyl)-N-methylamino]-5-pyridinecarboxylate was prepared from tert-butyl 2-[N-(2-benzyloxy-5-bromophenethyl)amino]-5-pyridinecarboxylate using a similar method to that of Example 1 but replacing iodoethane with iodomethane.
c. Crystallised from a $CH_2Cl_2$/diethyl ether/hexane mixture.
d. tert-Butyl 2-[N-(2-benzyloxy-5-bromophenethyl)-N-allylamino]-5-pyridinecarboxylate was prepared from tert-butyl 2-[N-(2-benzyloxy-5-bromophenethyl)amino]-5-pyridinecarboxylate using a similar method to that of Example 1 (E) but replacing iodoethane with allyl bromide.

EXAMPLE 43

4-[N-(2-Benzyloxy-5-bromophenethyl)-N-methylamino]benzoic acid (A) A mixture of ethyl 4-[N-(2-benzyloxy-5-bromophenethyl)-N-methylamino] benzoate (1.0 g) and 2N NaOH (5 ml) in ethanol (50 ml) was heated at reflux for 4 hours. The solution was evaporated, acidified with 2N HCl solution and the title product filtered off as a white powder (100%).

The starting material was prepared as follows:
(B) To a mixture of 2-benzyloxy-5-bromophenylacetic acid (3.2 g) in toluene (100 ml) was added thionyl chloride (1.0 ml) and DMF (3 drops ). The reaction was stirred at 80° C.

for 1 hour and cooled to ambient temperature. ethyl 4-aminobenzoate (2.0 g) and triethylamine (2 ml) were added to the reaction mixture with stirring. After standing for 18 hours, the mixture was diluted with dichloromethane and washed with water, 1N HCl solution, water and saturated aqueous NaHCO₃ solution. The organic extract was dried (MgSO₄), filtered and evaporated and the residue purified by trituration with diethyl ether to give ethyl 4-[2-benzyloxy-5-bromophenylacetamido]benzoate (2.0 g) mpt. 174°–176° C.

(C) A mixture of ethyl 4-[2-benzyloxy-5-bromophenylacetamido]-benzoate (2.5 g) and BH₃.THF (10 mM) in THF (60 ml) was stirred at 50° C. for 2 hours, cooled (ice bath) and diluted with 2N HCl solution (10 ml) and diethyl ether (50 ml). The organic layer was separated, dried (MgSO₄) amd evaporated. The residue was purified by chromatography on silica gel eluting with dichloromethane to give ethyl 4-[N-(2-benzyloxy-5-bromophenethyl)amino] benzoate (1.4 g).

(D) Ethyl 4-[N-(2-benzyloxy-5-bromophenethyl)amino] benzoate was converted to ethyl 4-[N-(2-benzyloxy-5-bromophenethyl)-N-methylamino]benzoate using a similar method to that described in Example 41(D) except methyl iodide was used in place of iodoethane.

EXAMPLE 44

4-[N-(2-Benzyloxy-5-bromophenethyl)amino]benzoic acid

The title compound was prepared from ethyl 4-[N-(2-benzyloxy-5-bromophenethyl)amino]benzoate using a similar method to that of Example 43(A).

EXAMPLE 45

N-Propyl-4-[N-(2-benzyloxy-5-bromophenethyl)-N-methylamino]benzamide and N-(3-pyridyl)-4-[N-(2-benzyloxy-5-bromophenethyl)-N-methylamino]-benzamide A mixture of 4-[N-(2-benzyloxy-5-bromophenethyl)-N-methylamino]benzoic acid (700 mg), triethylamine (0.6 ml) and oxalyl chloride (0.2 ml) in dichloromethane (50 ml) was stirred for 30 minutes. The solvent was evaporated and the residue dissolved in dichloromethane (60 ml). The resulting solution was divided into two portions. One portion was mixed with n-propylamine (0.5 ml) and the second with 3-aminomethylpyridine (0.5 ml). Each reaction was stirred for 1 hour, evaporated and the residues purified separately by chromatography on silica gel eluting the product of the first reaction with dichloromethane : ethyl acetate (4:1) and the second with ethyl acetate methanol (98:2). The first product, N-propyl-4-[N-(2-benzyloxy-5-bromophenethyl)-N-methylamino] benzamide (170 mg), was purified by crystallisation form dichloromethane/hexane mixtures. The second product, N-(3-pyridyl)-4-[N-(2-benzyloxy-5-bromophenethyl)-N-methylamino]-benzamide (100 mg) did not require further purification after chromatography.

EXAMPLE 46

4-[N-(2-(2-Benzyloxy-5-bromophenyl)ethyl)-N-ethylamino]benzoic acid

4-[N-(2-(2-benzyloxy-5-bromophenyl)ethyl)-N-ethylamino]-benzoic acid (mpt. 175° C.) was obtained from 2-benzyloxy-5-bromophenylacetic acid by a similar process to that described in Example 43.

EXAMPLE 47

4-[N-(2-(2-Benzyloxyphenyl)ethyl)-N-ethylamino]benzoic acid

Ethyl 4-[N-(2-(2-benzyloxyphenyl)ethyl)-N-ethylamino] benzoate was dissolved in a solution of methanol (20 ml) and tetrahydrofuran (20 ml). To this solution was added aqueous 2N sodium hydroxide (10.5 ml) and the mixture heated at reflux for 24 hours; cooled and the volume reduced by evaporation to half the original volume. Water (20 ml) was added and the mixture acidified with acetic acid. The resulting solid was filtered and dried under vacuum at 60° C. to give the title product (950mg) m.p. 175° C.

The starting material was prepared as follows:

2-Benzyloxyphenylacetic acid (5 g) was dissolved in dichloromethane and oxalyl chloride (2.6 g) added. Dimethyl formamide (2 drops) was added and the mixture was stirred at ambient temperature for 18 hours. The solvent was evaporated and the residue redissolved in dichloromethane (50 ml) and added to an ice cold solution of ethyl 4-(N-ethylamino)benzoate and triethylamine in dichloromethane (50 ml). The reaction mixture was allowed to warm to ambient temperature and washed with 2N hydrochloric acid (3×50 ml), aqueous sodium hydrogen carbonate solution (1×50 ml), dried over MgSO₄ and evaporated to give ethyl 4-[N-(2-benzyloxybenzylcarbonyl)-N-ethylamino]benzoate (8.1 g).

Ethyl 4-[N-(2-benzyloxybenzylcarbonyl)-N-ethylamino] benzoate (8.1 g) was dissolved in THF (20 ml) and 1M borane tetrahydrofuran complex added. The reaction mixture was heated at reflux for 1 hour and cooled. 2N Hydrochloric acid (20 ml) was added. The volume of the reaction mixture was reduced to half the original by evaporation. Water (100 ml) was added and made basic (pH 8) by the addition of solid potassium carbonate and the mixture extracted with diethyl ether (3×30 ml). The combined extracts were dried over MgSO₄ and evaporated. The residue was purified by MPLC, eluting with 1:1 dichloromethane/hexane, to give ethyl 4-[N-(2-(2-benzyloxyphenyl)ethyl)-N-ethylamino]benzoate (1.8 g) m.p. 76° C.

What we claim is:

1. A compound of the formula I;

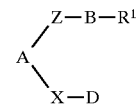

wherein:

A is an optionally substituted; and —X—D linking groups are positioned in a 1,2 relationship to one another on ring carbon atoms and the ring atom positioned ortho to the —X— linking group (and therefore in the 3-position relative to the —Z— linking group) is not substituted;

B is an optionally substituted: pyridyl, thiazolyl, oxazolyl, thienyl, thiadiazolyl, isoxazole, pyrazole, furyl, pyrrolyl, imidazolyl, pyrazinyl, pyridazinyl, pyrimidyl;

D is optionally substituted phenyl;

$R^1$ is positioned on ring B in a 1,3 or 1,4 relationship with the —Z— linking group and is carboxy or $R^1$ is of the formula —CONR$^a$ R$^{a1}$ wherein R$^a$ is hydrogen or $C_{1-6}$alkyl and R$^{a1}$ is hydrogen or optionally substituted: $C_{1-10}$alkyl, $C_{2-10}$alkenyl, $C_{2-10}$alkynyl, 5- or 6-membered heteroaryl or 5- or 6-membered heteroaryl$C_{1-6}$alkyl or $R^1$ is of the formula —CONHSO₂R$^b$ wherein R$^b$ is optionally substituted: $C_{1-10}$alkyl, $C_{2-10}$alkenyl, $C_{2-10}$alkynyl, 5- or 6-membered heteroaryl or phenyl;

X is —OCH₂-, —SCH₂-, —CH₂CH₂-, CH₂-, —O—, —S— or —N(R⁴)CH₂- wherein R⁴ is hydrogen or $C_{1-4}$alkyl and the left hand atom is attached to A and the right hand atom is attached to D;

Z is of the formula —CH($R^3$)CH($R^3$)N($R^2$)—, —N($R^2$)CH($R^3$)—, —CH($R^3$)$P^1$—, —(CH($R^3$))m— or —CH($R^3$)N($R^2$)— wherein $R^2$ is hydrogen, $C_{1-6}$alkyl (optionally substituted by hydroxy, cyano, nitro, amino, halo, $C_{1-4}$alkanoyl, $C_{1-4}$alkoxy or trifluoromethyl) $C_{2-6}$alkenyl, $C_{2-6}$alkynyl phenyl, or phenyl$C_{1-3}$alkyl;

$R^3$ is hydrogen or $C_{1-4}$alkyl;

$P^1$ is oxygen or sulphur, m is 2 or 3 and wherein the left hand atom is attached to A and the right hand atom is attached to B; provided that when Z is —CH($R^3$)N($R^2$)— or —(CH($R^3$))m—, X is not —OCH$_2$—; and N-oxides of —NR$^2$ where chemically possible; and S-oxides of sulphur containing rings where chemically possible; or a pharmaceutically acceptable salt or an in vivo hydrolysable ester or amide thereof.

2. A compound according to claim 1 which is:

N-hydroxyethyl-2-[N-ethyl-N-(2-(phenylethyl)benzyl)amino]pyridine-5-carboxamide;

N-propyl-2-[N-ethyl-N-(2-(phenylethyl)benzyl)amino]pyridine-5-carboxamide;

2-[N-ethyl-N-2-(phenethyl)benzyl)amino]pyridine-5-carboxylic acid;

2-[N-(5-bromo-2-(phenethyl)benzyl)-N-ethylamino]-5-pyridinecarboxylic acid;

2-[N-(2-(benzyl)benzyl)-N-ethylamino]-5-pyridinecarboxylic acid;

6-(N-ethyl-N-(2-phenoxybenzyl)amino)pyridazine-3-carboxylic acid;

2-(N-ethyl-N-(2-phenoxybenzyl)amino)pyridine-5-carboxylic acid;

6-(N-ethyl-N-(2-(benzylamino)benzyl)amino)pyridazine-3-carboxylic acid;

6-[N-(5-bromo-2-benzylaminobenzyl)-N-ethylamino]pyridazine-3-carboxylic acid;

2-[N-(2-benzyloxy-5-bromophenethyl)-N-ethylamino]-5-pyridinecarboxylic acid;

2-[N-(2-benzyloxy-5-bromophenethyl)amino]-5-pyridinecarboxylic acid;

2-[N-(2-benzyloxy-5-bromophenethyl)-N-methylamino]-5-pyridinecarboxylic acid; or 2-[N-(2-benzyloxy-5-bromophenethyl)-N-allylamino]-5-pyridinecarboxylic acid.

3. A compound according to claim 1 wherein B is optionally substituted pyridyl, thiazolyl, thienyl, pyridazinyl, thiadiazolyl, imidazolyl, pyrazinyl, pyrimidyl, or oxazolyl.

4. A compound according to claim 1 wherein D is optionally substituted phenyl.

5. A compound according to claim 1 wherein $R^1$ is carboxy or of the formula —CONR$^a$R$^{a1}$ or —CONHSO$_2$R$^b$.

6. A compound according to claim 1 wherein A is unsubstituted or substituted by halo, trifluoromethyl, nitro, hydroxy, amino, $C_{1-4}$alkylamino, di$C_{1-4}$alkylamino, cyano, $C_{1-6}$alkoxy, —S(O)$_p$C$_{1-6}$alkyl (p is 0, 1 or 2), $C_{1-6}$alkyl (optionally substituted by hydroxy, amino, halo, nitro or cyano), carbamoyl, $C_{1-4}$alkylcarbamoyl, di($C_{1-4}$alkyl)carbamoyl, $C_{1-4}$alkanoylamino, $C_{1-4}$alkanoyl(N—$C_{1-4}$alkyl)amino, $C_{1-4}$alkanesulphonamido or benzenesulphonamido.

7. A compound according to claim 1 wherein B is unsubstituted or substituted by halo, amino, $C_{1-4}$alkylamino, di($C_{1-4}$alkyl)amino, trifluoromethyl, nitro, hydroxy, $C_{1-6}$alkoxy or $C_{1-6}$alkyl.

8. A compound according to claim 1 wherein D is unsubstituted.

9. A process for preparing a compound according to claim 1 which comprises deprotecting a compound of the formula (III):

wherein $R^7$ is $R^1$ as defined in claim 1 or protected $R^1$, —$Z^1$— is —Z— as defined in claim 1 or protected —Z—, $R^2$, $R^3$, Z, X, A, B and D are as defined as defined in claim 1, and any optional substituents are optionally protected and at least one protecting group is present; and thereafter if necessary;

i) forming a pharmaceutically acceptable salt;

ii) forming an in vivo hydrolysable ester or amide;

iii) converting one optional substituent into another optional substituent.

10. A pharmaceutical composition comprising a compound according to claim 1 and a pharmaceutically-acceptable carrier.

11. A method of relieving pain by administering an effective amount of a compound of the formula (I) as defined in claim 1 to a patient in need thereof.

* * * * *

UNITED STATES PATENT AND TRADEMARK OFFICE
CERTIFICATE OF CORRECTION

PATENT NO. : 5,834,468
DATED : NOVEMBER 10, 1998
INVENTOR(S) : GLORIA ANNE BREAULT, ET AL.

It is certified that error appears in the above-indentified patent and that said Letters Patent is hereby corrected as shown below:

Column 1, line 31 - "oniates" should be — opiates —.

Column 1, line 34 - "NSAII)S" should be — NSAIDS —.

Column 4, line 61 - "$C_{5-7}$cycloalkenyl$C_{2-3}$" should be — $C_{5-7}$cycloalkenyl$C_{2-3}$alkynyl —.

Column 7, line 52 - "$C_{5-7}$cycloalkyl" should be — $C_{5-7}$cycloalkenyl —.

Column 9, line 51 - "ot-acyloxyalkyl" should be — α-acyloxyalkyl —.

Column 14, line 9 - "acting" should be — reacting —.

Column 14, line 38 - "-$N(R^3)CH(R^8)$-" should be — -$N(R^8)CH(R^3)$- —.

Column 15, line 18 - "ma,T" should be — may —.

Column 17, line 50 - "(VXA) should be — (IXA) —.

Column 22, line 34 - "it" should be — at —.

Column 30, line 12 - "(50 ml)" should be — (150 ml) —.

Column 39, line 65 - "020 C." should be — 0° —.

UNITED STATES PATENT AND TRADEMARK OFFICE
CERTIFICATE OF CORRECTION

PATENT NO. : 5,834,468
DATED : NOVEMBER 10, 1998
INVENTOR(S) : GLORIA ANNE BREAULT, ET AL.

It is certified that error appears in the above-indentified patent and that said Letters Patent is hereby corrected as shown below:

Column 41, line 19 - after "benzaldehyde" the word — acid — should be deleted.

Column 43, line 43 - after "benzoic" the word — acid — should be inserted.

Column 43, line 58 - "hexrine" should be — hexane —.

Column 46, line 60 - after "(m, 4H" the term — ); 4.30 — should be inserted.

Column 48, line 21 - "700° C." should be — 70° C. —.

Column 48, line 51 - "100° C." should be — 0° C. —.

Column 48, line 54 - after the word "the" — 20 — should be deleted.

In Claim 1, column 52, line 44, after "substituted" the words — phenyl; provided that the -Z-B-R$^1$ — should be inserted.

Signed and Sealed this

Sixth Day of March, 2001

Attest:

NICHOLAS P. GODICI

Attesting Officer

Acting Director of the United States Patent and Trademark Office